(12) United States Patent
Johansson et al.

(10) Patent No.: US 8,110,566 B2
(45) Date of Patent: Feb. 7, 2012

(54) THERAPEUTIC AGENTS 713

(75) Inventors: Lars Anders Mikael Johansson, Molndal (SE); Robert Andrew Judkins, Molndal (SE); Lanna Li, Molndal (SE); Bjorn Christian Ingvar Lofberg, Molndal (SE); Joachim Persson, Molndal (SE)

(73) Assignee: AstraZeneca AB, Sodertalje (SE)

( * ) Notice: Subject to any disclaimer, the term of this patent is extended or adjusted under 35 U.S.C. 154(b) by 91 days.

(21) Appl. No.: 12/771,594

(22) Filed: Apr. 30, 2010

(65) Prior Publication Data

US 2010/0280000 A1 Nov. 4, 2010

Related U.S. Application Data

(60) Provisional application No. 61/174,630, filed on May 1, 2009.

(51) Int. Cl.

| | | |
|---|---|---|
| A61K 31/4245 | (2006.01) | |
| A61P 3/04 | (2006.01) | |
| A61P 25/22 | (2006.01) | |
| A61P 25/24 | (2006.01) | |
| A61P 25/18 | (2006.01) | |
| A61P 25/28 | (2006.01) | |
| C07D 491/107 | (2006.01) | |

(52) U.S. Cl. ............... 514/210.16; 548/143; 548/950

(58) Field of Classification Search .................. None
See application file for complete search history.

(56) References Cited

U.S. PATENT DOCUMENTS

| | | | |
|---|---|---|---|
| 7,723,331 B2 | 5/2010 | Giordanetto et al. | 514/234.2 |
| 2005/0176795 A1 | 8/2005 | Schwink et al. | 514/384 |
| 2005/0222161 A1 | 10/2005 | Moriya et al. | 514/252.06 |
| 2008/0269275 A1 | 10/2008 | Brown et al. | 514/294 |
| 2008/0300232 A1 | 12/2008 | Brickmann et al. | 514/210.2 |
| 2008/0306055 A1 | 12/2008 | Egner et al. | 514/227.8 |
| 2009/0076064 A1 | 3/2009 | Urbanek et al. | 514/299 |

FOREIGN PATENT DOCUMENTS

| | | |
|---|---|---|
| EP | 1593667 | 11/2005 |
| JP | 2006176443 | 7/2006 |
| WO | WO 2004/004726 | 1/2004 |
| WO | WO 2005/066132 | 7/2005 |
| WO | WO 2005/070902 | 8/2005 |
| WO | WO 2005/090330 | 9/2005 |
| WO | WO 2006/019833 | 2/2006 |
| WO | WO 2006/044228 | 4/2006 |
| WO | WO 2006/066173 | 6/2006 |
| WO | WO 2006/068594 | 6/2006 |
| WO | WO 2006/125665 | 11/2006 |
| WO | WO 2006/130075 | 12/2006 |
| WO | WO 2007/011284 | 1/2007 |
| WO | WO 2007/078251 | 7/2007 |
| WO | WO 2008/011453 | 1/2008 |
| WO | WO 2008/020799 | 2/2008 |
| WO | WO 2008/068265 | 6/2008 |
| WO | WO 2008/076562 | 6/2008 |
| WO | WO 2008/131103 | 10/2008 |
| WO | WO 2009/024502 | 2/2009 |
| WO | WO 2009/052062 | 4/2009 |

OTHER PUBLICATIONS

Wuitschik et al., "Spirocyclic Oxetanes: synthesis and properties", Angew. Chem. Int. Ed. 47: 4512-4515 (2008).
International Search Report / Written Opinion for PCT/GB2010/050698, dated Jul. 30, 2010.

*Primary Examiner* — Yong Chu
(74) *Attorney, Agent, or Firm* — Morgan Lewis & Bockius LLP

(57) ABSTRACT

Disclosed herein are compounds of formula I

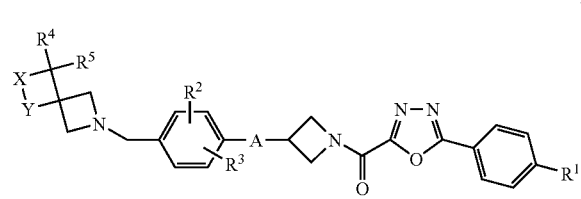

in which $R^1$, $R^2$, $R^3$, $R^4$, $R^5$, A, X, Y are as described in the specification, their use in pharmaceutical compositions and in methods of treatment or prophylaxis of a melanin-concentrating hormone related disease or condition.

23 Claims, No Drawings

THERAPEUTIC AGENTS 713

This application claims the benefit under 35 U.S.C. §119(e) of Application No. 61/174,630 (US) filed on 1 May 2009.

FIELD OF INVENTION

The present invention relates to certain (3-(4-(1- or 2-oxa-6-azaspiro[3.3]heptan-6-ylmethyl)phenoxy or phenylthio)azetidin-1-yl)(5-phenyl-1,3,4-oxadiazol-2-yl)methanone compounds of formula I, to processes for preparing such compounds and to intermediate compounds used in these processes, to their use in the treatment of a melanin-concentrating hormone related disease or condition for example obesity, obesity-related conditions, anxiety and depression, and to pharmaceutical compositions containing them.

BACKGROUND OF THE INVENTION

The actions of melanin-concentrating hormone (MCH) are thought to be involved in anxiety, depression, obesity, and obesity-related disorders. MCH has been found to be a major regulator of eating behaviour and energy homeostasis and is the natural ligand for the 353-amino acid orphan G-protein-coupled-receptor (GPCR) termed SLC-1 (also known as GPR24). SLC-1 is sequentially homologous to the somatostatin receptors, and is frequently referred to as the "melanin-concentrating hormone receptor" (MCH receptor type 1, MCH1 receptor, or MCHR1).

In mice lacking the MCH1 receptor, there is no increased feeding response to MCH, and a lean phenotype is seen, suggesting that this receptor is responsible for mediating the feeding effect of MCH. MCH receptor antagonists have also been shown to block the feeding effects of MCH, and to reduce body weight & adiposity in diet-induced obese mice. The conservation of distribution and sequence of MCH1 receptors suggest a similar role for this receptor in man and rodent species. Hence, MCH1 receptor antagonists have been proposed as a treatment for obesity and other disorders characterised by excessive eating and body weight.

Emerging evidence also suggests that MCHR1 plays a role in the regulation of mood and stress. Within the central nervous system, MCHR1 mRNA and protein are distributed in various hypothalamic nuclei including, for example, the paraventricular nucleus (PVN) and the nucleus accumbens shell; and limbic structures including, for example, the hippocampus, septum, amygdala, locus coeruleus and dorsal raphe nucleus, all of which are thought to be involved in the regulation of emotion and stress.

Introduction of MCH into the medial preoptic area has been reported to induce anxiety, although contrary anxiolytic-like effects of MCH injection have also been reported. Injection of MCH into the nucleus accumbens shell, in which MCHR1 is abundant, decreased mobility in a forced swim test in rats, suggesting a depressive effect. Also, it has been reported that MCHR1 antagonists exhibited antidepressant and anxiolytic-like effects in rodent tests, suggesting a role for MCHR1 in depression and anxiety.

MCH antagonists are thus thought likely to provide benefit to numerous people and to have a potential to alleviate anxiety and depression and be useful for treating obesity and obesity-related conditions.

The histamine H3 receptor is of current interest in developing new medicaments. The H3 receptor is a presynaptic autoreceptor located both in the central and peripheral nervous systems, the skin, and in organs, such as, for example, the lung, the intestine, probably the spleen, and the gastrointestinal tract. Recent evidence suggests the H3 receptor has intrinsic, constitutive activity in vitro as well as in vivo (i.e., it is active in the absence of an agonist). Compounds acting as inverse agonists can inhibit this activity. The histamine H3 receptor has been shown to regulate the release of histamine and also of other neurotransmitters, such as, for example, serotonin and acetylcholine. Some histamine H3 ligands, such as, for example, a histamine H3 receptor antagonist or inverse agonist may increase the release of neurotransmitters in the brain, whereas other histamine H3 ligands, such as, for example, histamine H3 receptor agonists may inhibit the biosynthesis of histamine, as well as, inhibit the release of neurotransmitters. This suggests that histamine H3 receptor agonists, inverse agonists, and antagonists could mediate neuronal activity. As a result, efforts have been undertaken to develop new therapeutics that target the histamine H3 receptor. It is believed that compounds that modulate histamine H3 receptors may be useful in treating cognitive deficiency, in schizophrenia, narcolepsy, obesity, Attention deficit hyperactivity disorder, pain and Alzheimer's disease.

SUMMARY OF THE INVENTION

The present invention provides compounds that are MCH1 receptor antagonists and therefore are likely to be useful in the treatment of anxiety, depression, obesity and obesity-related conditions. The compounds are also histamine H3 receptor modulators and may be useful in treating cognitive deficiency in schizophrenia, narcolepsy, Attention deficit hyperactivity disorder, pain and Alzheimer's disease. The compounds may also be particularly useful in the treatment of disorders when a dual action on the MCH and H3 receptors is desired, for example when treating obesity and obesity-related conditions.

DESCRIPTION OF THE INVENTION

The present invention provides a compound of formula I

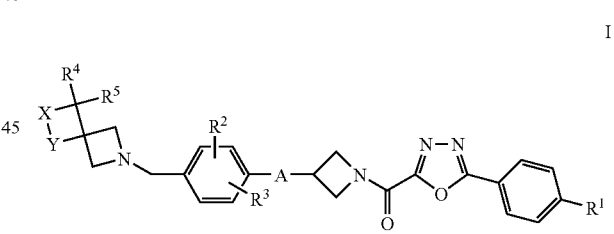

or a pharmaceutically acceptable salt thereof in which $R^1$ represents H, fluoro, chloro, bromo, cyano, a $C_{1-3}$alkyl group optionally substituted by one or more fluoro, or a $C_{1-2}$alkoxy group optionally substituted by one or more fluoro;

A represents O or S;

$R^2$ and $R^3$ independently represent H, fluoro, chloro, bromo, a $C_{1-4}$alkyl group optionally substituted by one or more fluoro, or a $C_{1-4}$alkoxy group optionally substituted by one or more fluoro; provided that $R^2$ and $R^3$ are not located meta to each other;

$R^4$ and $R^5$ independently represent H or a $C_{1-4}$alkyl group; and

X and Y independently represent O or $CH_2$ with the proviso that X and Y are different.

In another aspect the present invention provides a compound of formula IA

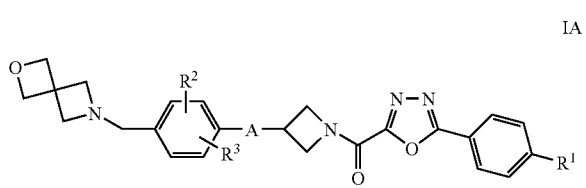

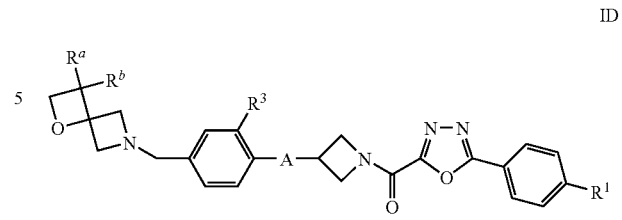

or a pharmaceutically acceptable salt thereof in which
$R^1$ represents H, fluoro, chloro, bromo, cyano, a $C_{1-3}$alkyl group optionally substituted by one or more fluoro, a $C_{1-2}$alkoxy group optionally substituted by one or more fluoro;
A represents O or S; and
$R^2$ and $R^3$ independently represent H, fluoro, chloro, bromo, a $C_{1-4}$alkyl group optionally substituted by one or more fluoro, or a $C_{1-4}$alkoxy group optionally substituted by one or more fluoro; provided that $R^2$ and $R^3$ are not located meta to each other.

In another aspect the present invention provides a compound of formula

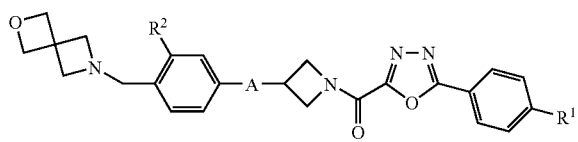

or a pharmaceutically acceptable salt thereof in which
$R^1$ represents H, chloro or a $C_{1-2}$alkoxy group optionally substituted by one or more fluoro;
A represents O or S; and
$R^2$ represents H or chloro.

In another aspect the present invention provides a compound of formula IC

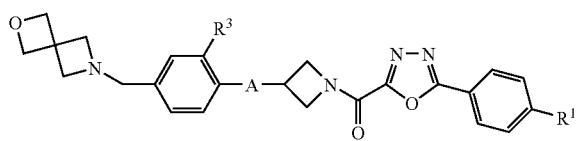

or a pharmaceutically acceptable salt thereof in which
$R^1$ represents H, chloro or a $C_{1-2}$alkoxy group optionally substituted by one or more fluoro;
A represents O or S; and
$R^3$ represents H or chloro.

In another aspect the present invention provides a compound of formula ID

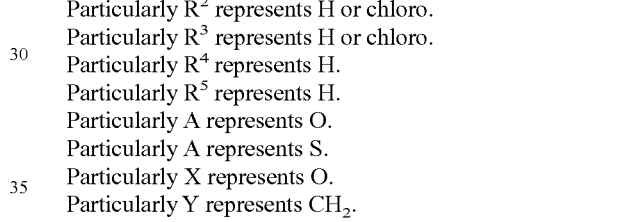

or a pharmaceutically acceptable salt thereof in which
$R^a$ and $R^b$ independently represent H or a $C_{1-4}$alkyl group;
$R^1$ represents H, chloro or a $C_{1-2}$alkoxy group optionally substituted by one or more fluoro;
A represents O or S; and
$R^3$ represents H or chloro.

Particular values of the substituents $R^a$, $R^b$, $R^1$, $R^2$, $R^3$, $R^4$, $R^5$, A, X, Y are now given. It will be understood that such values may be used where appropriate with any of the definitions, claims or embodiments defined hereinbefore or hereinafter, for example in any one of formulae I, IA, IB, IC or ID as appropriate.

Particularly $R^a$ represents H or methyl.
Particularly $R^b$ represents H or methyl.
Particularly $R^1$ represents H, chloro, fluoro, methoxy or difluoromethoxy.
Particularly $R^2$ represents H or chloro.
Particularly $R^3$ represents H or chloro.
Particularly $R^4$ represents H.
Particularly $R^5$ represents H.
Particularly A represents O.
Particularly A represents S.
Particularly X represents O.
Particularly Y represents $CH_2$.

The terms "$C_{1-4}$alkyl" refers to a straight or branched chain alkane radical containing from 1 to 4 carbon atoms. Exemplary groups include methyl; ethyl; propyl; isopropyl; 1-methylpropyl; n-butyl, t-butyl; and isobutyl.

The term "$C_{1-4}$ alkoxy" refers to groups of the general formula —$OR^a$, wherein $R^a$ is selected from a $C_{1-4}$alkyl. Exemplary alkoxys include, but are not limited to methoxy, ethoxy, propoxy, isopropoxy, butoxy, t-butoxy or isobutoxy.

In the remainder of this application the term formula I means a compound of formula I, or of formula IA, or of formula IB, or of formula IC or of formula ID unless otherwise stated.

In another aspect the present invention provides one or more of the following compounds:
(3-(4-(2-oxa-6-azaspiro[3.3]heptan-6-ylmethyl)-3-chlorophenoxy)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-chlorophenyl)-1,3,4-oxadiazol-2-yl)methanone;
(3-(4-(2-oxa-6-azaspiro[3.3]heptan-6-ylmethyl)phenoxy)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-methoxyphenyl)-1,3,4-oxadiazol-2-yl)methanone;
(3-(4-(2-oxa-6-azaspiro[3.3]heptan-6-ylmethyl)phenylthio)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-fluorophenyl)-1,3,4-oxadiazol-2-yl)methanone;

(3-(4-(2-oxa-6-azaspiro[3.3]heptan-6-ylmethyl)phenoxy)
azetidin-1-yl)(5-(4-(difluoromethoxy)phenyl)-1,3,4-oxa-
diazol-2-yl)methanone;
(3-(4-(2-oxa-6-azaspiro[3.3]heptan-6-ylmethyl)-2-chlo-
rophenoxy)azetidin-1-yl)(5-phenyl-1,3,4-oxadiazol-2-yl)
methanone;
(3-(4-((3,3-dimethyl-1-oxa-6-azaspiro[3.3]heptan-6-yl)me-
thyl)phenoxy)azetidin-1-yl)(5-(4-methoxyphenyl)-1,3,4-
oxadiazol-2-yl)methanone; and
(3-(2-chloro-4-((3,3-dimethyl-1-oxa-6-azaspiro[3.3]heptan-
6-yl)methyl)phenoxy)azetidin-1-yl)(5-phenyl-1,3,4-oxa-
diazol-2-yl)methanone;
or a pharmaceutically acceptable salt thereof.

It will be understood by those skilled in the art that the present invention may include any number of the above compounds between 1 and 10 inclusive. It will also be understood by those skilled in the art that the present invention encompasses a compound of formula I but excluding any one or more of the above-listed compounds.

Further described herein is a pharmaceutical composition comprising a compound of formula I, or a pharmaceutically acceptable salt thereof, and a pharmaceutically acceptable carrier and/or diluent.

Yet further described herein is a method for treatment or prophylaxis of a disease or condition in which modulation of the MCH1 receptor is beneficial comprising administering to a warm-blooded animal in need of such treatment or prophylaxis a therapeutically-effective amount of a compound of formula I, or a pharmaceutically acceptable salt thereof.

Yet still further described herein is using a compound according to formula I, or a pharmaceutically acceptable salt thereof, or mixtures thereof for the treatment or prophylaxis of a disease or condition in which modulation of the MCH1 receptor is beneficial.

Even further described herein is use of a compound according to formula I, or pharmaceutically acceptable salts thereof, or mixtures thereof in the manufacture of a medicament for the treatment or prophylaxis of a disease or condition in which modulation of the MCH1 receptor is beneficial.

Still further described herein is using a compound of formula I, or a pharmaceutically acceptable salt thereof, as a medicament.

In another aspect the present invention provides a compound of formula I for the treatment of a disease or condition in which modulation of the MCH1 receptor is beneficial, particularly obesity.

The term "MCHR" refers to the melanin-concentrating hormone receptor protein 1 (MCHR1), unless otherwise stated.

The terms "treat", "treating", and "treatment" refer to modulation of a disease and/or its attendant symptoms.

The terms "prevent", "preventing", and "prevention" refer to decreasing or eliminating a disease and/or its attendant symptoms.

The terms "modulate", "modulates", "modulating", or "modulation", as used herein, refer to, for example, the activation (e.g., agonist activity) or inhibition (e.g., antagonist activity) of an MCHR.

The term "pharmaceutically-acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The terms "prophylaxis", as used herein, refers to (i) preventing the development of a disease and/or condition; and/or (ii) protecting against worsening of a disease and/or condition in a situation where the disease and/or condition has developed.

As used herein, the term "MCHR-mediated condition or disease" refers to a condition or disease amenable to modulation by an MCHR active agent.

The term "therapeutically-effective amount" refers to that amount of a compound sufficient to modulate one or more of the symptoms of the condition or disease being treated.

A further embodiment relates to compounds as described herein wherein one or more of the atoms is a radioisotope of the same element, for example deuterium, $^{13}C$ or $^{14}C$. In a particular embodiment, the compound is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

A compound labeled with tritium may be useful in identifying novel medicinal compounds capable of binding to and modulating the activity, by agonism, partial agonism, or antagonism, of an MCH1 receptor. Such tritium-labeled compounds may be used in assays that measure the displacement of such compounds to assess the binding of ligands that bind to MCH1 receptors.

In an even further embodiment, compounds disclosed herein may additionally comprise one or more atoms of a radioisotope. In a particular form of this embodiment, a compound comprises a radioactive halogen. Such radio-labeled compounds are synthesized by incorporating radio-labeled starting materials by known methods. In a particular embodiment, the radioisotope is selected from $^{18}F$, $^{123}I$, $^{125}I$, $^{131}I$, $^{75}Br$, $^{76}Br$, $^{77}Br$ or $^{82}Br$. In a more particular embodiment, the radioisotope is $^{18}F$.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates, or mixtures thereof, of the compounds of formula I. The optically active forms of the compound of the invention may be prepared, for example, by chiral chromatographic separation of a racemate, by synthesis from optically active starting materials or by asymmetric synthesis based on the procedures described hereafter.

The compounds of the present invention may be purified in accordance with the general knowledge of one skilled in the art. Those techniques may be selected from for example crystallisation, slurrying or chromatography. Chromatographic methods may be selected from those using for instance reversed phase or normal phase techniques. The eluting solvent or solvent mixtures may be selected from those suitable for each technique.

It will further be understood that the present invention encompasses tautomers of the compounds of formula I.

It will be understood that certain compounds of the invention, including pharmaceutically acceptable salts thereof, may exist in solvated, for example hydrated, as well as unsolvated forms. It will further be understood that the present invention encompasses all such solvated forms of the compounds of formula I.

The compounds of formula I can also form salts. As a result, when a compound of formula I is referred to herein, such reference includes, unless otherwise indicated, salts thereof. In one embodiment, the compounds of formula I form pharmaceutically acceptable salts. In another embodiment, the compounds of formula I form salts that can, for example, be used to isolate and/or purify the compounds of formula I.

Generally, pharmaceutically acceptable salts of a compound in accordance with formula I can be obtained by using standard procedures well known in the art. These standard procedures include, but are not limited to, for example, the reacting of a sufficiently basic compound, such as, for example, an alkyl amine with a suitable acid, such as, for example, HCl or acetic acid, to afford a physiologically acceptable anion.

In one embodiment, a compound in accordance with formula I may be converted to a pharmaceutically acceptable salt or solvate thereof, particularly, an acid addition salt, such as, for example, hydrochloride, hydrobromide, phosphate, acetate, fumarate, maleate, tartrate, citrate, methanesulphonate, and p-toluenesulphonate.

In general, the compounds of formula I can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

The term "amino-protecting group" refers to art-recognized moieties capable of attaching to an amino group so as to prevent the amino group from taking place in reactions occurring elsewhere on the molecule containing the amino group. Acceptable amino-protecting groups, include but are not limited to, for example, amino-protecting groups described in "Protective Groups in Organic Synthesis", 2nd edition, John Wiley & Sons, 1991. The amino-protecting group may, for example, be a urethane type protective group (which is also referred to as a carbamate protective group), including but not limited to, for example, arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

Compounds of formula I may be prepared by a) reacting a compound of formula II

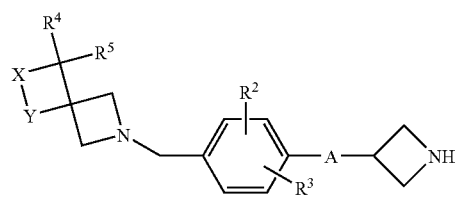

II in which A, X, Y, $R^2$, $R^3$, $R^4$ and $R^5$ are as previously defined with a compound of formula III

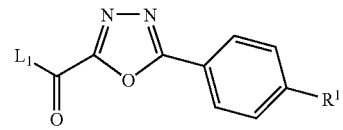

III in which $R^1$ is as previously defined and $L_1$ represents a leaving group for example a $C_{1-4}$alkoxy group, optionally in the presence of a solvent, for example ethanol, and at a temperature in the range of 0 to 150° C. particularly in the range of 50 to 120° C.; or b) reacting a compound of formula IV

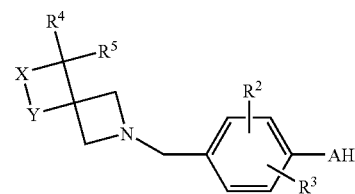

IV in which A, X, Y, $R^2$, $R^3$, $R^4$ and $R^5$ are as previously defined with a compound of formula V

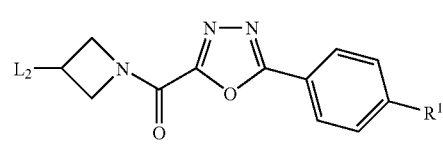

V in which $R^1$ is as previously defined and $L_2$ represents a leaving group, for example mesyloxy or tosyloxy, in the presence of a base, for example $Cs_2CO_3$, optionally in the presence of a solvent, for example DMF or preferably DMA, and at a temperature in the range of 0 to 150° C. particularly in the range of 50 to 120° C.; or c) reacting a compound of formula VI

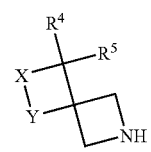

VI in which X, Y, $R^4$ and $R^5$ are as previously defined with a compound of formula VII

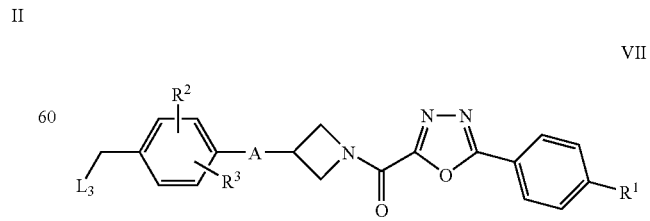

VII in which $R^1$, $R^2$, $R^3$ and A are as previously defined and $L_3$ represents a leaving group for example halo particularly chloro or bromo; optionally in the presence of a solvent, for example DMF, and optionally in the presence of a base for example an amine e.g. N-ethyl-N-isopropylpropan-2-amine at a temperature in the range of 0 to 150° C. particularly in the range of 5 to 50° C.; or d) reacting a compound of formula VI

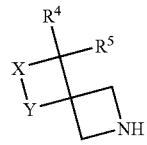

VI in which X, Y, $R^4$ and $R^5$ are as previously defined with a compound of formula XII

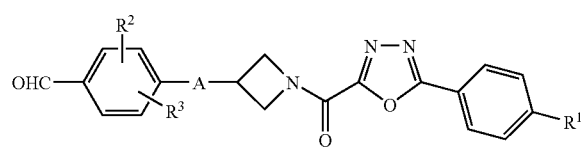

XII in which $R^1$, $R^2$, $R^3$ and A are as previously defined in the presence of a reducing agent, for example sodium triacetoxyborohydride, in an appropriate solvent, for example dichloromethane, and optionally in the presence of a base for example an amine e.g. N-ethyl-N-isopropylpropan-2-amine.

If the compound of formula III is an ester, then a compound of formula I can be obtained by reacting a compound of formula II and an ester of formula III optionally in the presence of a solvent, for example ethanol, and optionally in the presence of a catalyst such as sodium cyanide, and at a temperature in the range of 0 to 150° C. particularly in the range of 50 to 120° C. If a catalyst such as sodium cyanide is used then the temperature is preferably around ambient temperature for example 10 to 30° C.

Compounds of formulae II and IV may be prepared as shown in scheme 1 below and by methods analogous to those described in the examples.

Scheme 1

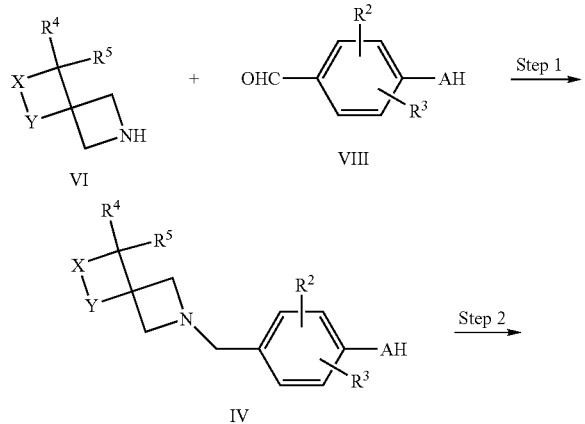

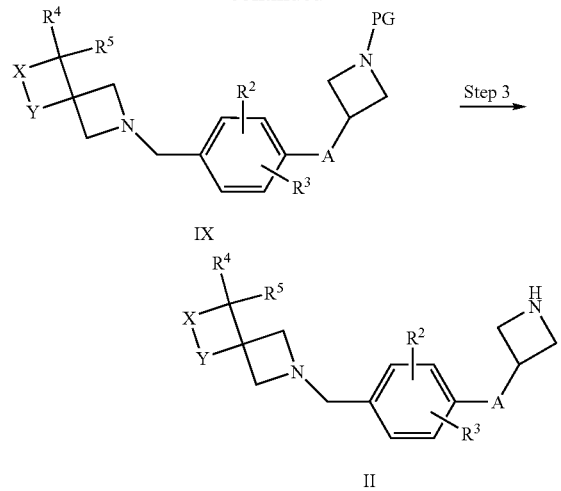

Step 1
A compound in accordance with formula IV can be obtained by reacting a compound of formula VI in which $R^4$ and $R^5$ are as previously defined with a benzaldehyde derivative of formula VIII in which A, $R^2$ and $R^3$ are as previously defined and a reducing agent, for example sodium triacetoxyborohydride, in an appropriate solvent, for example dichloromethane.

Step 2
A compound in accordance with formula IX can be obtained by reacting a compound of formula IV with an azetidine compound of formula X,

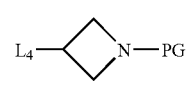

X in which PG represents an amine protecting group, for example tert-butoxycarbonyl and $L_4$ represents a leaving group, for example mesyloxy or tosyloxy in the presence of a base, for example, $Cs_2CO_3$, in the presence of an appropriate solvent, for example DMF.

Step 3
A compound in accordance with formula II can be obtained by treating a compound of formula IX with a deprotecting agent, for example HCl or TFA in an appropriate solvent, for example dichloromethane.

Compounds of formula III may be prepared according to well known procedures, as for instance to those described in *Journal fuer Praktische Chemie*, 327, 109-116 (1985), employing benzohydrazide compounds in accordance with formula XI,

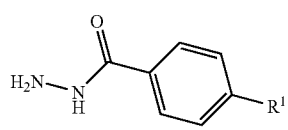

XI in which $R^1$ is as previously defined.

Compounds of formula V may be prepared as shown in scheme 2 below and by methods analogous to those described in the examples.

Scheme 2

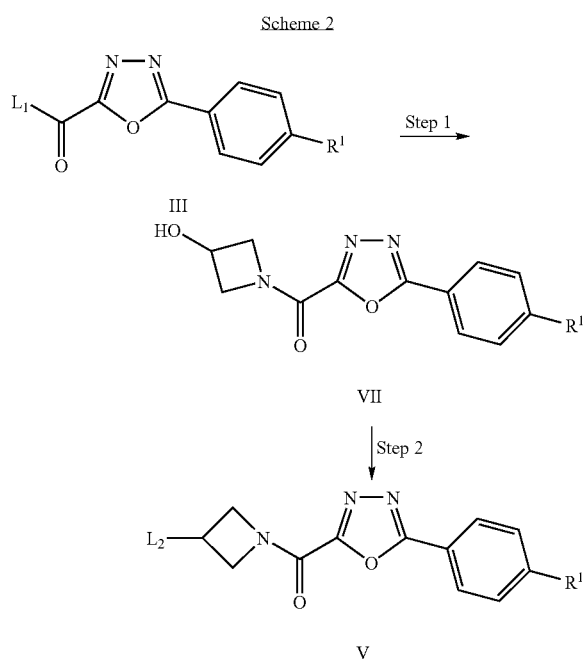

Step 1

A compound in accordance with formula VII can be obtained by reacting a compound of formula III in which $R^1$ is as previously defined with 3-hydroxyazetidine or a salt thereof in the presence of a base, for example triethylamine, optionally in the presence of a catalyst, for example sodium cyanide, in an appropriate solvent for example methanol.

Step 2

A compound in accordance with formula V can be obtained by treating a compound of formula VII with an alcohol activating agent for example methanesulfonyl chloride, in the presence of a base, for example triethylamine, in an appropriate solvent such as dichloromethane.

Compounds of formula VI may be prepared according to well known procedures, as for instance those described in *Angew. Chem. Int. Ed.*, 47, 4512-4515 (2008) and WO 2008/131103.

Compounds of formula VIII, X and XI are either commercially available or may readily be prepared according to well-known procedures for those skilled in the art.

Compounds of formula XII may be prepared by reacting a compound of formula V in which $R^1$ and $L_2$ are as previously defined with a compound of formula VIII in which $R^2$, $R^3$ and A are as previously defined in the presence of a base for example $Cs_2CO_3$, optionally in the presence of a solvent, for example DMF, and at a temperature in the range of 0 to 150° C. particularly in the range of 50 to 120° C.

Compounds or formulae II, IV, V, VII and XII are believed to be novel and are herein claimed as a further aspect of the present invention. In a preferred aspect of the invention these compounds are in substantially pure form e.g. greater than 50% pure, particularly greater than 95% pure and more particularly more than 99% pure.

Still yet an even further embodiment is directed to a method for treatment or prophylaxis of a disease or condition in which modulation of the MCH1 receptor is beneficial comprising administering to a warm-blooded animal in need of such treatment or prophylaxis a therapeutically effective amount of a compound of formula I or a pharmaceutically-acceptable salt thereof.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of a compound of formula I.

An even still further embodiment is directed to using a compound in accordance with formula I, or pharmaceutically acceptable salts thereof, or mixtures thereof for the treatment or prophylaxis of a disease or condition in which modulation of the MCH1 receptor is beneficial.

A more particular embodiment relates to using antagonistic-compounds of formula I, or pharmaceutically acceptable salts thereof, or mixtures thereof for the treatment or prophylaxis of a disease or condition in which modulation of the MCH1 receptor is beneficial.

Yet a further embodiment is directed to using a compound in accordance with formula I, or pharmaceutically acceptable salts thereof, or mixtures thereof in the manufacture of a medicament for the treatment or prophylaxis of a disease or condition in which modulation of the MCH1 receptor is beneficial.

Still yet a further embodiment is directed to using a compound in accordance with formula I, or pharmaceutically acceptable salts thereof, or mixtures thereof as a medicament.

Another embodiment is directed to a pharmaceutical composition comprising a compound in accordance with formula I, or pharmaceutically acceptable salts thereof, or mixtures thereof, and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or pharmaceutically-acceptable salt thereof, or mixtures thereof effective for treatment or prophylaxis of such disease or condition, and a pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

In one embodiment, the disease and/or condition for which a compound in accordance with formula I may be used for the treatment or prophylaxis includes, but is not limited to, for example, mood disorders, anxiety disorders, and eating disorders.

Exemplary mood disorders include, but are not limited to, for example, depressive disorder(s), such as, for example, major depressive disorder(s) and dysthymic disorder(s); bipolar depression and/or bipolar mania, such as, for example, bipolar I, including but not limited to those with manic, depressive or mixed episodes, and bipolar II; cyclothymiac's disorder(s); anxious depression; and mood disorder(s) due to a general medical condition.

Exemplary anxiety disorder(s) include, but are not limited to, for example, panic disorder(s) without agoraphobia; panic disorder(s) with agoraphobia; agoraphobia without history of panic disorder(s); specific phobia; social phobia; obsessive-compulsive disorder(s); stress related disorder(s); posttraumatic stress disorder(s); acute stress disorder(s); generalized anxiety disorder(s); and generalized anxiety disorder(s) due to a general medical condition.

Exemplary eating disorders, include, but are not limited to, for example, obesity.

Many of the above conditions and disorder(s) are defined for example in the American Psychiatric Association: Diagnostic and Statistical Manual of Mental Disorders, Fourth Edition, Text Revision, Washington, D.C., American Psychiatric Association, 2000.

Another embodiment is directed to a method for treatment or prophylaxis of a mood disorder, anxiety disorder, or eating disorder comprising administering to a warm-blooded animal in need of such treatment or prophylaxis a therapeutically effective amount of a compound according to formula I, or pharmaceutically acceptable salts, or mixtures thereof.

Yet another embodiment is directed to a method for treatment or prophylaxis of a mood disorder comprising administering to a warm-blooded animal in need of such treatment or prophylaxis a therapeutically effective amount of a compound according to formula I, or pharmaceutically acceptable salts, or mixtures thereof.

Still yet another embodiment is directed to a method for treatment or prophylaxis of an anxiety disorder comprising administering to a warm-blooded animal in need of such treatment or prophylaxis a therapeutically effective amount of a compound according to formula I, or pharmaceutically acceptable salts, or mixtures thereof.

Still an even further embodiment is directed to a method for treatment or prophylaxis of an eating disorder comprising administering to a warm-blooded animal in need of such treatment or prophylaxis a therapeutically effective amount of a compound according to formula I, or pharmaceutically acceptable salts, or mixtures thereof.

Another embodiment provides a method for treatment or prophylaxis of a disease or condition selected from anxiety, depression and obesity in a warm-blooded animal, comprising administering to said animal in need of such treatment or prophylaxis a therapeutically effective amount of a compound according to formula I.

Yet another embodiment provides a method for treatment or prophylaxis of anxiety in a warm-blooded animal, comprising administering to said animal in need of such treatment or prophylaxis a therapeutically effective amount of a compound according to formula I.

A further embodiment provides a method for treatment or prophylaxis of general anxiety disorder in a warm-blooded animal, comprising administering to said animal in need of such treatment or prophylaxis a therapeutically effective amount of a compound according to formula I.

Still yet another embodiment provides a method for treatment or prophylaxis of depression in a warm-blooded animal, comprising administering to said animal in need of such treatment or prophylaxis a therapeutically effective amount of a compound according to formula I.

Still yet an even further embodiment provides a method for treatment or prophylaxis of obesity in a warm-blooded animal, comprising administering to said animal in need of such treatment or prophylaxis a therapeutically effective amount of a compound according to formula I.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of an antagonistic compound of formula I.

A further embodiment is directed to a method for treatment or prophylaxis of a disease or condition selected from anxiety, depression and obesity in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of anxiety in a warm-blooded animal, comprising administering to said animal in need of such treatment or prophylaxis a therapeutically effective amount of a compound of formula I or a pharmaceutically-acceptable salt thereof.

Yet a further embodiment is directed to a method for treatment or prophylaxis of general anxiety disorder in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of depression in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of obesity in a warm-blooded animal, comprising administering to said animal in need of such treatment or prophylaxis a therapeutically effective amount of a compound of formula I or a pharmaceutically-acceptable salt thereof.

An even still further embodiment is directed to using a compound of formula I, or a pharmaceutically acceptable salt thereof, for the treatment or prophylaxis of a disease or condition in which modulation of the MCH1 receptor is beneficial.

A more particular embodiment relates to using antagonistic-compounds of formula I, or a pharmaceutically acceptable salt thereof, for the treatment or prophylaxis of a disease or condition in which modulation of the MCH1 receptor is beneficial.

A further embodiment is directed to using a compound of formula I, or a pharmaceutically acceptable salt thereof for the treatment or prophylaxis of a disease or condition selected from mood disorder, anxiety disorder, and eating disorder.

A still further embodiment is directed to using a compound of formula I, or a pharmaceutically acceptable salt thereof, for the treatment or prophylaxis of mood disorder.

An even further embodiment is directed to using a compound of formula I, or a pharmaceutically acceptable salt thereof for the treatment or prophylaxis of anxiety disorder.

An even still further embodiment is directed to using a compound of formula I, or a pharmaceutically acceptable salt thereof, for the treatment or prophylaxis of an eating disorder.

Yet a still further embodiment is directed to using a compound of formula I, or a pharmaceutically acceptable salt thereof, for the treatment or prophylaxis of a disease or condition selected from anxiety, depression and obesity.

Still yet a further embodiment is directed to using a compound of formula I, or a pharmaceutically acceptable salt thereof, for the treatment or prophylaxis of anxiety.

Yet still a further embodiment is directed to using a compound of formula I, or a pharmaceutically acceptable salt thereof, for the treatment or prophylaxis of general anxiety disorder.

Even still yet a further embodiment is directed to using a compound of formula I, or a pharmaceutically acceptable salt thereof, or mixtures thereof for the treatment or prophylaxis of depression.

Yet another embodiment is directed to using a compound of formula I, or a pharmaceutically acceptable salt thereof, for the treatment or prophylaxis of obesity.

Yet a further embodiment is directed to using a compound of formula I, or a pharmaceutically acceptable salt thereof, in the manufacture of a medicament for the treatment or prophylaxis of a disease or condition in which modulation of the MCH1 receptor is beneficial.

A further embodiment is directed to using a compound of formula I, or a pharmaceutically acceptable salt thereof, in the manufacture of a medicament for the treatment or prophylaxis of a disease or condition selected from mood disorder, anxiety disorder, and eating disorder.

Yet a further embodiment is directed to using a compound of formula I, or a pharmaceutically acceptable salt thereof, in the manufacture of a medicament for the treatment or prophylaxis of mood disorder.

A still further embodiment is directed to using a compound of formula I, or a pharmaceutically acceptable salt thereof, in the manufacture of a medicament for the treatment or prophylaxis of anxiety disorder.

Still yet a further embodiment is directed to using a compound of formula I, or a pharmaceutically acceptable salt thereof, in the manufacture of a medicament for the treatment or prophylaxis of an eating disorder.

An even further embodiment is directed to using a compound of formula I, or a pharmaceutically acceptable salt thereof, in the manufacture of a medicament for the treatment or prophylaxis of a disease or condition selected from anxiety, depression and obesity.

A still even further embodiment is directed to using a compound of formula I, or a pharmaceutically acceptable salt thereof, in the manufacture of a medicament for the treatment or prophylaxis of anxiety.

A yet even further embodiment is directed to using a compound of formula I, or a pharmaceutically acceptable salt thereof, in the manufacture of a medicament for the treatment or prophylaxis of general anxiety disorder.

A yet still even further embodiment is directed to using a compound of formula I, or a pharmaceutically acceptable salt thereof, in the manufacture of a medicament for the treatment or prophylaxis of depression.

Another embodiment is directed to using a compound of formula I, or a pharmaceutically acceptable salt thereof, in the manufacture of a medicament for the treatment or prophylaxis of obesity.

A further embodiment is directed to using a compound of formula I, or a pharmaceutically acceptable salt thereof, for the treatment or prophylaxis insulin resistance, hepatic steatosis (including NASH), fatty liver, or sleep apnea.

Still yet a further embodiment is directed to using a compound of formula I, or a pharmaceutically acceptable salt thereof, as a medicament.

Even further described herein is the use of compounds of formula I, or diastereomers or enantiomers thereof, or pharmaceutically acceptable salts of formula I or diastereomers or enantiomers thereof, or mixtures thereof in the manufacture of a medicament for the therapy of a disorder selected from cognitive deficient in schizophrenia, narcolepsy, obesity, Attention deficit hyperactivity disorder, pain, and Alzheimer's disease.

Still further described herein is the use of compounds of formula Ic, or diastereomers or enantiomers thereof, or pharmaceutically acceptable salts of formula Ic or diastereomers or enantiomers thereof, or mixtures thereof in the manufacture of a medicament for the therapy of a disorder selected from cognitive deficient in schizophrenia, narcolepsy, obesity, Attention deficit hyperactivity disorder, pain, and Alzheimer's disease.

Yet even further described herein is a pharmaceutical composition comprising a compound according to formula I or Ic, or diastereomers or enantiomers thereof, or pharmaceutically acceptable salts of formula I or Ic, or diastereomers or enantiomers thereof, or mixtures thereof and a pharmaceutically acceptable carrier and/or diluent.

Still even further described herein is a method for treating a disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of a compound according to formula I or Ic, or diastereomers, enantiomers, or mixtures thereof, or pharmaceutically acceptable salts of formula I or Ic, or diastereomers, enantiomers, or mixtures thereof.

Still yet even further described herein is a method for treating a disorder in which modulating the histamine H3 receptor is beneficial comprising administering to a warm-blooded animal in need of such treatment a therapeutically effective amount of a compound according to formula I or Ic, or diastereomers, enantiomers, or mixtures thereof, or pharmaceutically acceptable salts of formula I or Ic, or diastereomers, enantiomers, or mixtures thereof.

Another embodiment is directed to a pharmaceutical composition comprising a compound of formula I, or a pharmaceutically acceptable salt thereof, and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or a pharmaceutically-acceptable salt thereof, effective for treatment or prophylaxis of such disease or condition, and a pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

Yet another embodiment provides a process for preparing a compound of Formula I.

In still yet another embodiment, a compound of formula I, or a pharmaceutically acceptable salt thereof, and/or a pharmaceutical composition or formulation comprising a compound of formula I, or a pharmaceutically acceptable salt thereof, may be administered concurrently, simultaneously, sequentially or separately with an other pharmaceutically active compound selected from the following:

(i) antidepressants, including, but not limited to, for example, agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine, and equivalents and pharmaceutically active isomer(s) and metabolite(s) thereof;

(ii) atypical antipsychotics including, but not limited to, for example, quetiapine, and pharmaceutically active isomer(s) and metabolite(s) thereof;

(iii) antipsychotics including, but not limited to, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and metabolite(s) thereof;

(iv) anxiolytics including, but not limited to, for example, alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam, and equivalents and pharmaceutically active isomer(s) and metabolite(s) thereof;

(v) anticonvulsants including, but not limited to, for example, carbamazepine, valproate, lamotrogine, gabapentin, and equivalents and pharmaceutically active isomer(s) and metabolite(s) thereof;

(vi) Alzheimer's therapies including, but not limited to, for example, donepezil, memantine, tacrine, and equivalents and pharmaceutically active isomer(s) and metabolite(s) thereof;

(vii) Parkinson's therapies including, but not limited to, for example, deprenyl, L-dopa, Requip, Mirapex, MAOB inhibitors such as selegeline and rasagiline, comP inhibitors such as Tasmar, A-2 inhibitors, dopamine reuptake inhibitors, NMDA antagonists, Nicotine agonists, Dopamine agonists, inhibitors of neuronal nitric oxide synthase, and equivalents and pharmaceutically active isomer(s) and metabolite(s) thereof;

(viii) migraine therapies including, but not limited to, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including, but not limited to, for example, abciximab, activase, NXY-059, citicoline, crobenetine, desmoteplase, repinotan, traxoprodil, and equivalents and pharmaceutically active isomer(s) and metabolite(s) thereof;

(x) urinary incontinence therapies including, but not limited to, for example, darafenacin, falvoxate, oxybutynin, propiverine, robalzotan, solifenacin, tolterodine, and equivalents and pharmaceutically active isomer(s) and metabolite(s) thereof;

(xi) neuropathic pain therapies including, but not limited to, for example, gabapentin, lidoderm, pregablin, and equivalents and pharmaceutically active isomer(s) and metabolite(s) thereof;

(xii) nociceptive pain therapies including, but not limited to, for example, celecoxib, etoricoxib, lumiracoxib, rofecoxib, valdecoxib, diclofenac, loxoprofen, naproxen, paracetamol, and equivalents and pharmaceutically active isomer(s) and metabolite(s) thereof;

(xiii) insomnia therapies including, but not limited to, for example, agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem, and equivalents and pharmaceutically active isomer(s) and metabolite(s) thereof;

(xiv) mood stabilizers including, but not limited to, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof;

(xv) insulin and insulin analogues;

(xvi) insulin secretagogues including sulphonylureas (for example glibenclamide, glipizide), prandial glucose regulators (for example meglitindes e.g. repaglinide and nateglinide);

(xvii) dipeptidyl peptidase IV inhibitors (for example saxagliptin, sitagliptin, alogliptin or vildagliptin);

(xviii) insulin sensitising agents including PPARgamma agonists (for example pioglitazone and rosiglitazone), and agents with combined PPARalpha and gamma activity;

(xix) agents that modulate hepatic glucose balance (for example biguanides e.g. metformin, fructose 1,6 bisphosphatase inhibitors, glycogen phosphorylase inhibitors, glycogen synthase kinase inhibitors);

(xx) agents designed to reduce the absorption of glucose from the intestine (for example alpha glucosidase inhibitors e.g. acarbose);

(xxi) agents that prevent the reabsorption of glucose by the kidney (for example SGLT-2 inhibitors for example dapagliflozin);

(xxii) agents designed to treat the complications of prolonged hyperglycaemia (for example aldose reductase inhibitors);

(xxiii) an anti-obesity compound, for example orlistat (EP 129 748) or sibutramine (GB 2,184,122 and U.S. Pat. No. 4,929,629);

(xxiv) anti-dyslipidaemia agents such as, HMG—CoA reductase inhibitors (eg statins for example rosuvastatin); PPARα agonists (fibrates, e.g. fenofibrate, clofibrate and gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);

(xxv) antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);

(xxvi) haemostasis modulators such as, antithrombotics, activators of fibrinolysis; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;

(xxvii) agents which antagonise the actions of glucagon;

(xxviii) anti-inflammatory agents, such as non-steroidal anti-inflammatory drugs (eg. aspirin) and steroidal anti-inflammatory agents (eg. cortisone);

(xxix) an antihypertensive compound, for example an angiotensin converting enzyme (ACE) inhibitor, an angiotensin II receptor antagonist, an adrenergic blocker, an alpha adrenergic blocker, a beta adrenergic blocker, a mixed alpha/ beta adrenergic blocker, an adrenergic stimulant, calcium channel blocker, an AT-1 receptor blocker, a saluretic, a diuretic or a vasodilator;

(xxx) a PDK inhibitor;
(xxxi) a phytosterol compound;
(xxxii) an 11β HSD-1 inhibitor;
(xxxiii) an UCP-1, 2 or 3 activator;
(xxxiv) a CB1 receptor modulator for example an inverse agonist or an antagonist e.g. rimonabant or taranabant;
(xxxv) an NPY receptor modulator; for example an NPY agonist or an NPY2 agonist or an NPY5 antagonist;
(xxxvi) an MC4r modulator for example an MC4r agonist;
(xxxvii) an MC3r modulator for example an MC3r agonist;
(xxxviii) an orexin receptor modulator for example an antagonist;
(xxxix) modulators of nuclear receptors for example LXR, FXR, RXR, GR, ERRα, β, PPARα, β, γ, δ and RORalpha;
(xl) a DGAT1 inhibitor;
(xli) a DGAT2 inhibitor;
(xlii) a DGAT2 anti-sense oligonucleotide;
(xliii) a fatty acid synthase inhibitor
(xliv) a CETP (cholesteryl ester transfer protein) inhibitor;
(xlv) a cholesterol absorption antagonist;
(xlvi) a MTP (microsomal transfer protein) inhibitor;
(xlvii) probucol;
(xlviii) a GLP-1 agonist;
(xlix) a glucokinase modulator
l) a ghrelin antibody;
li) a ghrelin antagonist;
lii) a GPR119 agonist and
liii) another melanin concentrating hormone (MCH) modulator for example an MCH-1 antagonist;
or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

The above other pharmaceutically active compound, when employed in combination with the compounds of formula I, or pharmaceutically acceptable salts thereof, or mixtures thereof may be used, for example, in the amounts indicated in the Physicians' Desk Reference (PDR) or as otherwise determined by one of ordinary skill in the art.

For the uses, methods, medicaments and compositions mentioned herein the amount of formula I compound, or pharmaceutically acceptable salts thereof, or mixtures thereof used and the dosage administered may vary with the formula I compound, or pharmaceutically acceptable salts, or mixtures thereof employed; and/or the desired mode of administration and/or treatment. However, in general, satisfactory results are obtained when a compound in accordance with formula I, or pharmaceutically acceptable salts, or mixtures thereof is administered at a daily dosage of about 0.1 mg to about 20 mg/kg of animal body weight. Such doses may be given in divided doses 1 to 4 times a day or in a sustained release form. For man, the total daily dose may, for example, range of from about 5 mg to about 1,400 mg, and more particularly from about 10 mg to about 100 mg. Unit dosage forms suitable for oral administration generally comprise, for example, from about 2 mg to about 1,400 mg of a compound in accordance with formula I, or pharmaceutically acceptable salts, or mixtures thereof admixed with a solid and/or liquid pharmaceutical carrier, lubricant, and/or diluent.

The specific dose level and frequency of dosage for any particular subject, however, may vary and generally depends on a variety of factors, including, but not limited to, for example, the bioavailability of the specific formula I compound(s), or pharmaceutically acceptable salts, or mixtures thereof in the administered form; metabolic stability and length of action of the specific formula I compound(s), or pharmaceutically acceptable salts, or mixtures thereof; species, age, body weight, general health, sex, and diet of the subject; mode and time of administration; rate of excretion; drug combination; and severity of the particular condition.

Compound(s) in accordance with formula I, or pharmaceutically acceptable salts, or mixtures thereof may be administered by any means suitable for the condition to be treated and the quantity of formula I, or pharmaceutically acceptable salts, or mixtures thereof to be delivered.

Compound(s) in accordance with formula I, or pharmaceutically acceptable salts, or mixtures thereof may be administered in the form of a conventional pharmaceutical composition by any route including, but not limited to, for example, orally, intramuscularly, subcutaneously, topically, intranasally, epidurally, intraperitoneally, intrathoracially, intravenously, intrathecally, intracerebroventricularly, and injecting into the joints.

In one embodiment, the route of administration is orally, intravenously or intramuscularly.

A compound of formula I, or pharmaceutically acceptable salts, or mixtures thereof may be used on their own or in the form of appropriate medicinal preparations for enteral or parenteral administration.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, a solid, a liquid, and mixtures thereof The solid carrier can also be a diluent, flavoring agent, solubilizer, lubricant, suspending agent, binder, encapsulating material, and/or table disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with a finely divided compound of formula I, or pharmaceutically acceptable salts, or mixtures thereof.

A tablet can be prepared by, for example, mixing a compound in accordance with formula I, or pharmaceutically acceptable salts, or mixtures thereof in suitable proportions with a pharmaceutically acceptable carrier having the necessary binding properties and compacted into the desired shape and size.

A suppository can be prepared by, for example, mixing a compound of formula I, or pharmaceutically acceptable salts, or mixtures thereof with a suitable non-irritating excipient that is liquid at rectal temperature but solid at a temperature below rectal temperature, wherein the non-irritating excipient is first melted and the formula I compound dispersed therein. The molten homogeneous mixture is then poured into convenient sized molds and allowed to cool and solidify. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions.

Exemplary liquid pharmaceutical compositions suitable for parenteral administration include, but are not limited to, for example, sterile water or water propylene glycol solutions of a compound in accordance with formula I, or pharmaceutically acceptable salts, or mixtures thereof; and aqueous polyethylene glycol solutions of a compound in accordance with formula I, or pharmaceutically acceptable salts, or mixtures thereof.

Aqueous solutions for oral administration can be prepared by dissolving a compound in accordance with formula I, or pharmaceutically acceptable salts, or mixtures thereof in water and adding suitable colorants, flavoring agents, stabilizers, and/or thickening agents as desired.

Aqueous suspensions for oral administration can be prepared by dispersing a finely divided compound of formula I, or pharmaceutically acceptable salts, or mixtures thereof in water together with a viscous material, such as, for example, a natural synthetic gum, resin, methyl cellulose, and sodium carboxymethyl cellulose.

In one embodiment, the pharmaceutical composition contains from about 0.05% to about 99% w (percent by weight) of a compound in accordance with formula I, or pharmaceutically acceptable salts, or mixtures thereof. All percentages by weight are based on total composition.

In another embodiment, the pharmaceutical composition contains from about 0.10% to about 50% w (percent by weight) of a compound in accordance with formula I, or pharmaceutically acceptable salts, or mixtures thereof. All percentages by weight are based on total composition.

Also provided herein is a process for preparing a pharmaceutical composition comprising mixing or compounding the ingredients together and forming the mixed ingredients into tablets or suppositories; encapsulating the ingredients in capsules; or dissolving the ingredients to form injectable solutions.

Assay Methods:
MCH Binding Assay:

Binding of Melanin Concentrating Hormone (MCH) may be measured with a radioligand-binding assay employing [$^{125}$I]MCH and membranes expressing human Melanin Concentrating Hormone receptor 1 (MCHR1). Ligands that bind to MCHR1 may be identified by their ability to compete with the binding of [$^{125}$I]MCH.

[$^{125}$I]MCH may be purchased from Perkin Elmer (NEK373050UC 25 μCi). Membranes (2.20 mg/mL) may be prepared from CHOK1 cells expressing human MCH receptor 1 such as those obtainable from EuroScreen. Trizma, BSA, NaCl, and $MgCl_2 6H_2O$ may be purchased from Sigma. Human MCH may be purchased from Bachem (0.5 mg, cat #H-1482).

Saturation binding assays may be run in 50 mM Tris, pH 7.4, containing 3 mM $MgCl_2$ and 0.05% BSA. To perform an assay, 100 μL of 2-fold serially diluted radioligand [$^{125}$I] MCH is added to wells of a shallow 96-well plate. This is followed by addition of 100 μL of assay buffer containing membranes at a final protein concentration of 20 μg/mL. The mixture is incubated at room temperature for 1 h before being filtered through a Wallac A-filter treated with 0.1% PEI using a cell harvester (Skatron). Collected membranes are washed 3 times with 300 μL/well of wash buffer (50 mM Tris, pH 7.4, containing 5 mM $MgCl_2$ and 50 mM NaCl), and then dried in air overnight or at 60° C. $^{125}$I is measured by scintillation counting.

[$^{125}$I]MCH binding assays performed in the presence of test compounds, either at fixed or a series of concentrations, may be employed in a ligand competition binding assay. For dose-response assays, compounds may be 3-fold serially diluted in an assay plate to produce a range of concentrations. For single point assays, [$^{125}$I]MCH and membranes may be pre-mixed and then transferred to an assay plates with respective final membrane protein and radioligand concentrations of 20 μg/mL and 0.04 nM.

For analysis of data from saturation binding, cpm are converted to dpm, and nM radioligand concentration is calculated using vendor-provided specific radioactivity.

Saturation binding data may be analyzed using equation (1):

$$B = \frac{B_{max}[[^{125}I]MCH]}{K_d + [[^{125}I]MCH]} \quad (1)$$

where B is concentration of bound ligand, $B_{max}$ is the maximum concentration of bound ligand, and $K_d$ is the dissociation constant for ligand.

Percent inhibition (% Inh) may be calculated using equation (2):

$$\% \, Inh = 100 \bigg/ \left(1 - \frac{(counts_{sample} - counts_{negative})}{(counts_{positive} - counts_{negative})}\right) \quad (2)$$

$IC_{50}$ values may be calculated by conventional methods using non-linear squares analysis.

MCHR1 Receptor Activation Assay:

Melanin Concentrating Hormone Receptor 1 (MCHR1) is a G-protein coupled receptor that interacts with heterotrimeric G proteins containing a $G\alpha_{i/o}$ subunit. Binding of MCH to MCHR1 results in the exchange of GDP for GTP on the $G\alpha_{i/o}$ proteins associated with the activated receptor. This activation can be quantified by measuring the amount of a GTP analog, GTPγ$^{35}$S, bound to the membrane-associated receptor. GTPγ$^{35}$S is not hydrolyzed by the intrinsic GTPase activity of a G-protein but instead forms a stable complex. Activation of MCH1 receptors may thus be quantified by measuring the amount of GTPγ$^{35}$S bound to membranes prepared from cells expressing such receptors. Membranes may be isolated by filtration or may be bound on SPA beads (Amersham). Bound GTPγ$^{35}$S may then be quantified by determining the amount of $^{35}$S present. Inhibition of MCH binding by a competing ligand may thus be assessed by a decrease in the amount of GTPγ$^{35}$S bound to membranes in the presence of such a competing ligand.

Histamine $H_3$ SPA with the Agonist Radioligand [$^3$H]—N-α-methylhistamine

The H3 binding assay was/can be used to evaluate the ability of a compound of the invention to inhibit [$^3$H]—N-α-methylhistamine binding to CHO—K1 membranes expressing human histamine H3 receptors (full-length H3, the most prevalent brain isoform 445). In 200 μl 96-well SPA format, human H3 membranes (12.5 μg protein/well) and 1.4 nM [$^3$H]—N-α-methylhistamine were/can be incubated with a compound of the invention for 1.5 hrs to determine percent effect with respect to total (1% DMSO) and non-specific binding (10 μM imetit). Reproducibility of the assay is such that $IC_{50}$ curves can be generated in singlicate. Single poke (SP) testing can be done in triplicate.

Membranes, prepared from CHO—K1 cells stably expressing the human histamine H3 receptor, can be obtained from ACS.

Tested formulae I, IA and/or IB compounds were/can be provided as solubilized samples in neat DMSO. Serial dilutions were/can be performed in DMSO.

Plates were/can be 96-well Unifilter GF/B (Perkin Elmer, 6005177). Plates were/can be read on a Perkin Elmer TopCount. CPM data was/can be used to analyze unless DPM data generated by a quench curve was/is required.

Prep Work 1. 1 mg/mL BSA was/can be added to assay buffer (AB) on day of assay.
2. Amounts required for bead/membrane pool in AB were/can be calculated: "P"—need 17.1 mL/assay plate+10 mL PlateMate excess. Buffer volume was/can be split between beads and membranes to allow for polytroning of membranes prior to addition to beads.
   a. PVT-WGA SPA Beads: beads (P×9.83 mg/mL) were/can be resuspended for 1750 µg/well final. A minimum of 15 minutes was/can be waited prior to adding membranes (See b. below.).
   b. Membranes (hH3 membranes from CHO cells containing recombinant human H3 receptors, 11.7 mg/mL): membranes were/can be removed from −80° C. and thawed in RT waterbath. (0.0702 mg/mL×P) mg of membranes were/can be resuspended in the remaining volume not used with beads above for 12.5 µg/well final and homogenized briefly at polytron speed 5.0. The homogenized membrane mixture was/can be combined with the beads and a minimum of 30 minutes was/can be waited prior to dispensing to plate.
3. Formulae I, IA and/or IB, compounds: For Single Poke, 2 µl 1 mM of a compound in accordance with formula I, IA and/or IB was/can be dispensed to Optiplates (triplicate plates) for final a concentration of 10 µM. (CMA dispensed 2.41 of 0.909 mM.) For $IC_{50}$, 6 µl of a compound in accordance with formula I, IA and/or IB was/can be placed in DMSO in column 1 of a 96-well 500 µl polypropylene U-bottom plate for top final concentration of 10 µM. Imetit (see below) was/can be used as a control.
4. Imetit (for NSB and control): a 100 µM solution in DMSO was/can be prepared for a final assay concentration of 1 µM (NSB) or 100 nM ($IC_{50}$).
5. [$^3$H]—N-α-methylhistamine ([$^3$H]—NAMH): A solution in AB at 14 nM, 10× final concentration of 1.4 nM was/can be prepared. 5 µl samples were/can be calculated in quadruplicate on the β counter. If concentration was/is 12-14.5 nM, no adjustment was/is may be required. (For $IC_{50}$s, use final concentration on calculation tab of ABase template.)

Assay

1. For $IC_{50}$s: a compound in accordance with formulae I, IA and/or IB was/can be diluted 1:10 in DMSO (6 µl+54 µl DMSO was/can be added by PlateMate), and 1:3 serial dilutions (30 µl+60 µl) were/can be prepared in DMSO for a top final dilution of 1:1000 from stock concentration.
2. 2 µl of the formulae I, IA and/or IB compound dilution was/can be mixed and then transferred into assay plates. DMSO was/can be removed and 2 µl of 100 µM Imetit was/can be added to the wells.
3. 178 µl bead/membrane mixture was/can be dispensed into the assay plate.
4. 20 µl [$^3$H]—NAMH was/can be added with Rapid Plate. The assay plate was/can be sealed and incubated for 1.5 hr on RT shaker at speed ~6.5.
5. The assay plate was/can be subsequently centrifuged at 1000 rpm for 10 minutes.
6. The count was/can be performed on TopCount using one of the 3H SPA H3 Quench programs.

The DPM data was/can be analyzed when tSIS was/is less than that associated with 70% of full scale on the quench curve (tSIS<25%). Otherwise, CPM data was/is used. A typical window was/is 800-1200 CPM total, 45-70 CPM NSB (Z' 0.70-0.90).

The Data can be analyzed by calculating percent effect {average of [1-(singlicate minus plate NSB)/(plate Total minus plate NSB)]×100%}, $IC_{50}$, and Ki using the Cheng-Prusoff equation below and an ActivityBase or XLfit template.

$$Ki = \frac{IC_{50}}{1+([\text{ligand}]/Kd)} \text{ where}$$

$Kd$ is the value for the [$^3H$] ligand(0.67 nM)

In this assay, the ligand can be adjusted to 1.4 nM, which is ~2× the average Kd (0.67 nM).

The $IC_{50}$ and nH can be determined by fitting the data to model 205 in XLfit: y=A+((B−A)/(1+((C/x)^D)).

Guanosine 5'-O-(3-[$^{35}$S]thio)triphosphate [GTPγS] Binding Assay

A GTPγS binding assay can be used to investigate antagonist properties of compounds in CHO cells (Chinese Hamster Ovary) transfected with human Histamine H3 receptor (hH3R). Membranes from CHO cells expressing hH3R (10 µg/well) are diluted in GTPγS assay buffer (20 mM Hepes, 10 mM MgCl$_2$, 100 mM NaCl, pH 7.4) and preincubated with saponine (3 µg/mL), GDP (10 µM) and PVT-WGA SPA beads (125 µg/well) (Amersham) for 30 minutes. To determine antagonist activity, (R)-α-methyl histamine (30 nM) is added in 96 well SPA plate with [$^{35}$S]GTPγS (0.2 nM) and various concentration of H3R antagonists. The GTPγS binding assay is started with addition of the mixture membrane/saponine/GDP and incubated for 90 minutes at room temperature. The amount of bound [$^{35}$S]GTPγS is determined by using the MicroBeta Trilux counter (PerkinElmer). The percentage of [$^{35}$S]GTPγS bound in each sample is calculated as a percentage of that bound control sample incubated in absence of H3 antagonist. Duplicate determinations are obtained for each concentration, and the data are analyzed using ExcelFit4 to obtain the $IC_{50}$.

$IC_{50}$ Values

The $IC_{50}$ values for the Example compounds are set forth in Table 1 hereinbelow.

At least one compound of the present invention has an $IC_{50}$ value of less than about 100 µM. In a further embodiment, at least one compound of the present invention has an activity in at least one of the above referenced assays with an $IC_{50}$ value of between about 1 nm to about 100 µM. In an even further embodiment, at least one compound of the present invention has activity in at least one of the above referenced assays with an $IC_{50}$ value of between about 2 nM to about 100 nM. In yet a further embodiment, at least one compound of the present invention has activity in at least one of the above referenced assays with an $IC_{50}$ value of between about 2 nM and 50 nM. In one embodiment, at least one compound of the present invention has activity in at least one of the above referenced assays via an $IC_{50}$ value of less than about 100 nM. In another embodiment, at least one compound of the present invention has activity in at least one of the above referenced assays with an $IC_{50}$ value of less than about 50 nM. In yet another embodiment, at least one compound of the present invention has activity in at least one of the above referenced assays with an $IC_{50}$ value of less than about 20 nM.

Set forth in Table 1 hereinbelow are $IC_{50}$ values that were generated in accordance with the histamine $H_3$ SPA Assay as essentially described hereinabove and/or GTPγS Binding Assay as essentially described hereinabove.

TABLE 1

| Example No. | MCHr1 IC$_{50}$ (nM) | H3 IC$_{50}$ (μM) |
|---|---|---|
| 1 | 17 | 0.41 |
| 2 | 10 | 0.62 |
| 3 | 23 | 0.80 |
| 4 | 27 | 0.50 |
| 5 | 17 | |
| 6 | 24 | |
| 7 | 12 | |
| 8 | 24 | |
| 9 | 27 | |
| 10 | 30 | |

Examples

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

In general, the compounds of Formula I can be prepared in accordance with the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art. Combinatorial techniques can be employed in the preparation of compounds, for example, where the intermediates possess groups suitable for these techniques.

The following abbreviations are employed herein: APCI: atmospheric pressure chemical ionization; aq.: aqueous; DMA: N,N-dimethylacetamide; DMSO: dimethyl sulfoxide; DMF: N,N-dimethylformamide; h: hour(s); RP HPLC: reversed phase high performance liquid chromatography; K$_2$CO$_3$: potassium carbonate; LC: liquid chromatography; MgSO$_4$: magnesium sulfate; min: minutes; MS: mass spectrum; NaCl: Sodium chloride; NaHCO$_3$: sodium bicarbonate; Na$_2$SO$_4$: Sodium sulfate; Cs$_2$CO$_3$: caesium carbonate; NH$_3$: Ammonia; NMR: nuclear magnetic resonance; d: doublet; dd: double doublet; t: triplet; MHz: megahertz; sat.: saturated; TFA: trifluoroacetic acid.

LC/MS HPLC method: Waters Acquity UPLC Column Acquity UPLC BEH C18, 1.7 um, 2.1×100 mm. Gradient 5-95% acetonitrile in ammonium carbonate buffer at pH10 (40 mM NH$_3$+6.5 mM H$_2$CO$_3$) in 5.8 minutes at 60° C. Flow 0.8 mL/min.

Chemical IUPAC names are generated by software provided by CambridgeSoft Corporation, Cambridge, Mass. 02140, USA.

Example 1

(3-(4-(2-Oxa-6-azaspiro[3.3]heptan-6-ylmethyl)-3-chlorophenoxy)azetidin-1-yl)(5-phenyl-1,3,4-oxadiazol-2-yl)methanone

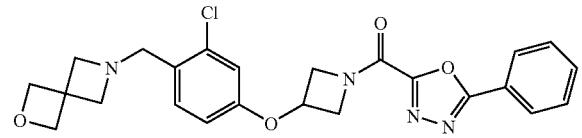

1A. 4-(2-Oxa-6-azaspiro[3.3]heptan-6-ylmethyl)-3-chlorophenol

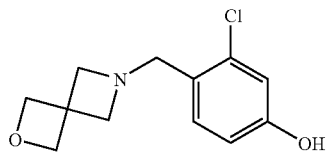

To a solution of 2-chloro-4-hydroxy-benzaldehyde (0.50 g, 3.19 mmol) in dichloromethane (35 mL) was added 2-oxa-6-azaspiro[3.3]heptane hemioxalate—for preparation, see e.g. Angew. Chem. Int. Ed., 47, 4512-4515 (2008)—(0.55 g, 3.83 mmol). After stirring for 20 min, sodium triacetoxyborohydride (1.01 g, 4.79 mmol) was added and the reaction mixture was stirred overnight. The mixture was diluted with dichloromethane and transferred to a separatory funnel. Water was added and the organic phase was separated off. The aqueous phase was saturated with K$_2$CO$_3$ and then extracted three times with dichloromethane. The combined organic layers were dried (phase separator) and concentrated in vacuo. There was obtained 0.65 g (85%) of 1A as a solid. $^1$H NMR (500 MHz, CDCl$_3$): δ 3.51 (s, 4H), 3.62 (s, 2H), 4.74 (s, 4H), 6.55 (d, 1H), 6.71 (d, 1H), 7.09 (d, 1H), MS (APCI+) m/z 240 [M+H]$^+$.

1B. (3-Hydroxyazetidin-1-yl)(5-phenyl-1,3,4-oxadiazol-2-yl)methanone

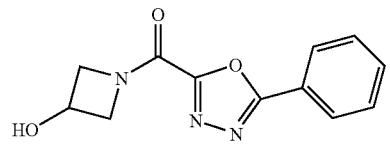

To a clear solution of ethyl 5-phenyl-1,3,4-oxadiazole-2-carboxylate (0.40 g, 1.83 mmol) in dry methanol (5 mL) was added sodium cyanide (18 mg, 0.37 mmol). A solution of 3-hydroxyazetidine hydrochloride (0.45 g, 2.84 mmol) and triethylamine (0.40 mL, 2.84 mmol) in methanol (5 mL) was added at ambient temperature. After stirring for 20 min water (20 mL) and dichloromethane (30 mL) were added. The layers were separated and the aqueous phase was extracted twice with dichloromethane (30 mL). The combined organic layers were evaporated. The crude product was then treated with toluene (5 mL), filtered, washed with toluene (5 mL) and dried in vacuo. There was obtained 0.40 g (90%) of 1B as a solid. $^1$H NMR (400 MHz, DMSO-d$_6$): δ 3.84 (dd, 1H), 4.31 (m, 2H), 4.56 (m, 1H), 4.79 (dd, 1H), 5.87 (d, 1H), 7.64 (m, 3H), 8.05 (d, 2H), MS (APCI+) m/z 246 [M+H]$^-$.

1C. 1-(5-Phenyl-1,3,4-oxadiazole-2-carbonyl)azetidin-3-yl methanesulfonate

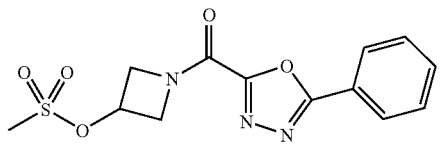

A suspension of 1B (2.00 g, 8.16 mmol) in dichloromethane (200 mL) was cooled in an ice-bath. Triethylamine (1.58 mL, 11.42 mmol) was added followed by methanesulfonyl chloride (0.85 mL, 11.01 mmol). After the addition, the cooling bath was removed. The mixture was stirred overnight and then transferred to a separatory funnel. The mixture was washed with water and then with aqueous NaHCO$_3$. The organic solution was dried (phase separator) and evaporated. There was obtained 2.58 g (98%) of 1C as a solid. $^1$H NMR (500 MHz, CDCl$_3$): δ 3.13 (s, 3H), 4.43 (dd, 1H), 4.64 (dd, 1H), 4.87 (dd, 1H), 5.12 (dd, 1H), 5.40 (m, 1H), 7.54 (t, 2H), 7.59 (t, 1H), 8.15 (d, 2H), MS (APCI+) m/z 324 [M+H]$^+$.

1. (3-(4-(2-Oxa-6-azaspiro[3.3]heptan-6-ylmethyl)-3-chlorophenoxy)azetidin-1-yl)(5-phenyl-1,3,4-oxadiazol-2-yl)methanone 1A (0.30 g, 1.25 mmol) was dissolved in dry DMF (10 mL) and 1C (0.61 g, 1.88 mmol) was added followed by Cs$_2$CO$_3$ (0.82 g, 2.50 mmol). The reaction mixture was stirred at 90° C. for 24 h. The mixture was filtered and approximately half the volume of solvent was evaporated. The product was purified by preparative RP HPLC (gradient: 15-55% acetonitrile over 30 min, 0.2% ammonia buffer). The pure fractions were combined and concentrated. Dichloromethane was added and the solution was dried (phase separator) and concentrated in vacuo. There was obtained 0.26 g (44.5%) of 1 as a solid. $^1$H NMR (500 MHz, CDCl$_3$): δ 3.57 (s, 4H), 3.73 (s, 2H), 4.33 (d, 1H), 4.65 (dd, 1H), 4.73 (m, 1H), 4.77 (s, 4H), 5.06 (m, 1H), 5.14 (dd, 1H), 6.70 (d, 1H), 6.80 (s, 1H), 7.37 (m, 1H), 7.54 (m, 2H), 7.59 (m, 1H), 8.16 (d, 2H), MS (APCI+) m/z 467 [M+H]$^+$. LC purity: 96%. A slurry experiment was performed by weighing 2.5 mg of Example 1 into a vial and adding ethanol (100 µL). The slurry was shaken for 7 days at ambient temperature and then crystals were collected using a small spatula. The crystals were dried in a hood for one hour and then analyzed using DSC (differential scanning calorimetry). A sample was weighed into an aluminium pan with a pierced lid and heated from 0° C. to 300° C. with a ramp of 5° C./min and modulated with the amplitude of ±0.6° C. every 45 seconds. The instrument was purged with nitrogen at 50 mL/minute; melting point 119±5° C.

Example 2

(3-(4-(2-Oxa-6-azaspiro[3.3]heptan-6-ylmethyl)phenoxy)azetidin-1-yl)(5-(4-chlorophenyl)-1,3,4-oxadiazol-2-yl)methanone

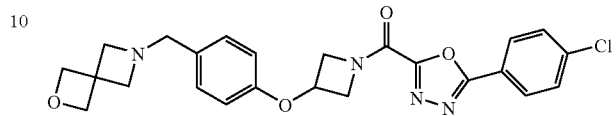

2A.
4-(2-Oxa-6-azaspiro[3.3]heptan-6-ylmethyl)phenol

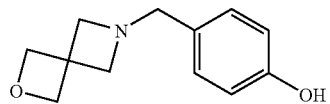

2-Oxa-6-azaspiro[3.3]heptane hemioxalate—for preparation, see e.g. *Angew. Chem. Int. Ed.,* 47, 4512-4515 (2008)—(2.0 g, 13.9 mmol) and 4-hydroxybenzaldehyde (1.7 g, 13.9 mmol) were mixed together with dichloromethane. The suspension was stirred at room temperature for 30 min and then sodium triacetoxyborohydride (3.8 g, 18.0 mmol) was added in small portions. The mixture was stirred at room temperature for 18 h, then diluted with dichloromethane and transferred to a separatory funnel. The mixture was extracted with water and K$_2$CO$_3$ was added in small portions to the aqueous phase until saturation. The solution was extracted several times with dichloromethane. The combined organic solutions were dried over Na$_2$SO$_4$ and then the solvent was removed by evaporation. There was obtained 2.2 g (77%) of 2A as an oil. $^1$H NMR (500 MHz, CDCl$_3$): δ 3.41 (s, 4H), 3.48 (s, 2H), 4.72 (s, 4H), 6.64 (d, 2H), 7.04 (d, 2H), MS (APCI+) m/z 206 [M+H]$^-$.

2B. (5-(4-Chlorophenyl)-1,3,4-oxadiazol-2-yl)(3-hydroxyazetidin-1-yl)methanone

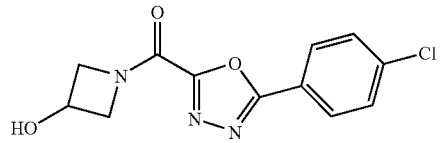

To a suspension of ethyl 5-(4-chlorophenyl)-1,3,4-oxadiazole-2-carboxylate—for preparation, see e.g. WO 97/05131—(0.53 g, 2.10 mmol) in dry methanol (10 mL) was added sodium cyanide (20 mg, 0.42 mmol). A solution of 3-hydroxyazetidine hydrochloride (0.38 g, 2.78 mmol) and triethylamine (0.39 mL, 2.78 mmol) in methanol (10 mL) was added at ambient temperature. The mixture was stirred for 2.5 h. Water (30 mL) was added and the mixture was extracted with dichloromethane. The organic layers were combined and evaporated to a white solid, which was treated with toluene (5 mL) and then filtered. The product was washed with toluene (5 mL) and then dried in vacuo. There was obtained 0.52 g (90%) of 2B as a solid. $^1$H NMR (400 MHz, CD$_3$OD): δ 4.00 (dd, 1H), 4.46 (dd, 2H), 4.70 (m, 1H), 4.93 (dd, 1H), 7.62 (d, 2H), 8.11 (d, 2H), MS (APCI+) m/z 280 [M+H]$^+$.

2C. 1-(5-(4-Chlorophenyl)-1,3,4-oxadiazole-2-carbonyl)azetidin-3-yl methanesulfonate

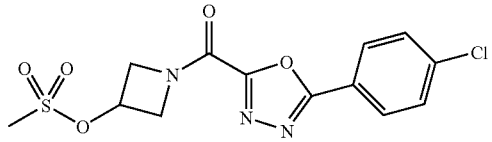

A suspension of 2B —which contained approximately 50% of methyl 5-(4-chlorophenyl)-1,3,4-oxadiazole-2-carboxylate as an impurity—(1.38 g, 2.47 mmol) in dichloromethane (50 mL) was cooled in an ice-bath. Triethylamine (0.51 mL, 3.70 mmol) was added followed by methanesulfonyl chloride (0.27 mL, 3.45 mmol). After the addition, the cooling bath was removed. The mixture was stirred for 7 h. The reaction mixture was transferred to a reparatory funnel and was washed with water followed by aqueous NaHCO$_3$. The organic solution was dried (phase separator) and evaporated. Dichloromethane (50 mL) and diethyl ether (200 mL) were added and the solid product was collected by filtration. The solid was washed twice with diethyl ether and then dried in vacuo. The product was purified using flash column chromatography first eluting with dichloromethane and then with a mixture of dichloromethane and methanol containing 2M NH$_3$ (20:1). There was obtained 0.66 g (75%) of 2C as a solid. $^1$H NMR (500 MHz, CDCl$_3$): δ 3.13 (s, 3H), 4.43 (dd, 1H), 4.65 (dd, 1H), 4.87 (dd, 1H), 5.12 (dd, 1H), 5.41 (m, 1H), 7.53 (d, 2H), 8.10 (d, 2H), MS (APCI+) m/z 358 [M+H]$^+$.

2. (3-(4-(2-Oxa-6-azaspiro[3.3]heptan-6-ylmethyl) phenoxy)azetidin-1-yl)(5-(4-chlorophenyl)-1,3,4-oxadiazol-2-yl)methanone The title compound was prepared using a similar protocol as described in Example 1 employing 2A and 2C as starting materials. There was obtained 70 mg (12%) of 2 as an oil. The oil gradually solidified on standing in room temperature. $^1$H NMR (500 MHz, CDCl$_3$): δ 3.41 (s, 4H), 3.53 (s, 2H), 4.34 (d, 1H), 4.65 (m, 1H), 4.74 (s, 5H), 5.09 (m, 1H), 5.14 (m, 1H), 6.73 (d, 2H), 7.21 (d, 2H), 7.52 (d, 2H), 8.10 (d, 2H), MS (APCI+) m/z 467 [M+H]$^-$, LC purity: 92%.

A slurry experiment was performed by weighing 10.5 mg of Example 2 into a vial and adding ethanol (168 μL). The slurry was shaken for 7 days at ambient temperature and then crystals were collected using a small spatula. The crystals were dried in a hood for one hour and then analyzed using DSC (differential scanning calorimetry). A sample was weighed into an aluminium pan with a pierced lid and heated from 0° C. to 300° C. with a ramp of 5° C./min and modulated with the amplitude of ±0.6° C. every 45 second. The instrument was purged with nitrogen at 50 mL/minute; melting points 128±5° C. and 138±5° C.

Example 3

(3-(4-(2-Oxa-6-azaspiro[3.3]heptan-6-ylmethyl)phenoxy)azetidin-1-yl)(5-phenyl-1,3,4-oxadiazol-2-yl) methanone

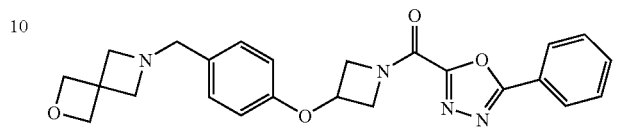

3A. tert-Butyl 3-(4-(2-oxa-6-azaspiro[3.3]heptan-6-ylmethyl)phenoxy)azetidine-1-carboxylate

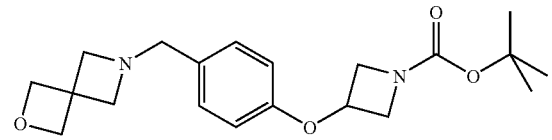

2A (0.77 g, 3.75 mmol) was dissolved in dry DMF (20 mL) and Cs$_2$CO$_3$ (2.44 g, 7.50 mmol) was added. The reaction mixture was stirred at room temperature for 10 min and then tert-butyl 3-(methylsulfonyloxy)azetidine-1-carboxylate (1.88 g, 7.50 mmol) was added. The reaction mixture was thereafter stirred at 90° C. for 24 h. The mixture was filtered and the solvent was evaporated. The residue was dissolved in DMSO (6 mL) and purified by preparative RP HPLC (gradient: 15-55% acetonitrile over 30 min, 0.2% ammonia buffer). The pure fractions were combined and concentrated. Dichloromethane was added and the solution was dried (phase separator) and concentrated. There was obtained 1.00 g (74%) of 3A as an oil which solidified on standing at room temperature. $^1$H NMR (500 MHz, CDCl$_3$): δ 1.45 (s, 9H), 3.34 (s, 4H), 3.46 (s, 2H), 3.99 (dd, 2H), 4.28 (dd, 2H), 4.73 (s, 4H), 4.84 (m, 1H), 6.68 (d, 2H), 7.15 (d, 2H), MS (APCI+) m/z 361 [M+H]$^-$.

3B. 6-(4-(Azetidin-3-yloxy)benzyl)-2-oxa-6-azaspiro [3.3]heptane

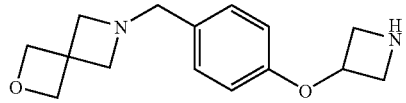

3A (0.19 g, 0.52 mmol) was dissolved in dichloromethane (20 mL) and TFA (1.95 mL, 26 mmol) was added. The reaction mixture was stirred at room temperature for two hours. K$_2$CO$_3$ (5 g) was added in portions and the mixture was stirred for 20 min. A saturated solution of K$_2$CO$_3$ (aq) was added and the mixture was transferred to a separatory funnel. The layers were separated and the aqueous layer was further extracted several times with dichloromethane. The combined organic solutions were dried (phase separator) and evaporated. There was obtained 128 mg (94%) of 3B as an oil. $^1$H NMR (500 MHz, CDCl$_3$): δ 3.34 (s, 4H), 3.45 (s, 2H), 3.80 (m, 2H), 3.92 (m, 2H), 4.72 (s, 4H), 4.98 (m, 1H), 6.69 (d, 2H), 7.13 (d, 2H), MS (APCI+) m/z 261 [M+H]$^+$.

3. (3-(4-(2-Oxa-6-azaspiro[3.3]heptan-6-ylmethyl) phenoxy)azetidin-1-yl)(5-phenyl-1,3,4-oxadiazol-2-yl)methanone 3B (0.30 g, 1.15 mmol) was mixed with ethyl 5-phenyl-1, 3,4-oxadiazole-2-carboxylate (0.30 g, 1.38 mmol) in a microwave vial and sealed. The solid mixture was melted in a preheated oil bath and stirred at 120° C. for 4 h. DMSO (2 mL) was added and the mixture was filtered, and then purified by preparative RP HPLC (gradient: 15-55% acetonitrile over 25 min, 0.2% ammonia buffer). The pure fractions were combined and then evaporated. Dichloromethane was added and the solution was dried (phase separator) and concentrated in vacuo. There was obtained 0.30 g (61%) of 3 as a colorless oil. The oil gradually solidified on standing in room temperature. $^1$H NMR (500 MHz, CDCl$_3$): δ 3.38 (s, 4H), 3.49 (s, 2H), 4.31 (d, 1H), 4.65 (m, 1H), 4.73 (s, 5H), 5.06 (m, 1H), 5.11 (m, 1H), 6.72 (d, 2H), 7.19 (d, 2H), 7.47-7.63 (m, 3H), 8.14 (d, 2H), MS (APCI+) m/z 433 [M+H]$^+$, LC purity: 97%.

Example 4

(3-(4-(2-Oxa-6-azaspiro[3.3]heptan-6-ylmethyl)phenoxy)azetidin-1-yl)(5-(4-methoxyphenyl)-1,3,4-oxadiazol-2-yl)methanone

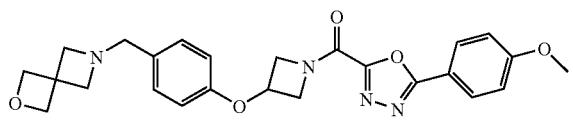

4A. (3-Hydroxyazetidin-1-yl)(5-(4-methoxyphenyl)-1,3,4-oxadiazol-2-yl)methanone

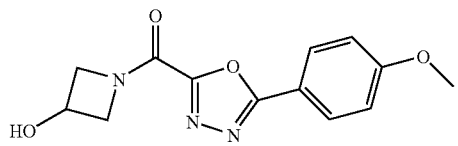

To a suspension of ethyl 5-(4-methoxyphenyl)-1,3,4-oxadiazole-2-carboxylate—see e.g. *Journal fuer Praktische Chemie*, 327, 109-116 (1985)—(0.50 g, 2.01 mmol) in dry methanol (10 mL) was added sodium cyanide (20 mg, 0.40 mmol). A solution of 3-hydroxyazetidine hydrochloride (0.26 g, 2.42 mmol) in methanol (2 mL) and then triethylamine (0.34 mL, 2.42 mmol) were added at ambient temperature. The reaction mixture was stirred at ambient temperature overnight. Water (20 mL) and dichloromethane (30 mL) were added. Some of the desired product precipitated and was filtered off. The two layers after filtration were separated and the aqueous phase was extracted twice with dichloromethane (30 mL). The combined organic layers were dried over MgSO$_4$ and the solution was evaporated. In total, there was obtained 0.43 g (77%) of 4A as a solid. $^1$H NMR (400 MHz, DMSO-d$_6$): δ 3.82 (dd, 1H), 3.84 (s, 3H), 4.30 (m, 2H), 4.55 (m, 1H), 4.77 (dd, 1H), 5.85 (d, 1H), 7.16 (d, 2H), 7.98 (d, 2H), MS (APCI+) m/z 276 [M+H]$^+$.

4B. 1-(5-(4-Methoxyphenyl)-1,3,4-oxadiazole-2-carbonyl)azetidin-3-yl methanesulfonate

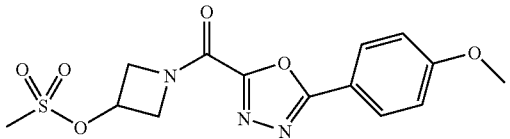

A suspension of 4A (5.45 g, 19. 8 mmol) in dichloromethane (100 mL) was cooled in an ice-bath. Triethylamine (4.4 mL, 31.7 mmol) was added followed by methanesulfonyl chloride (2.3 mL, 29.7 mmol). After the addition, the cooling bath was removed. The mixture was stirred for 7 h. The mixture was transferred to a separatory funnel and was washed with water followed by aqueous NaHCO$_3$ (sat.). The organic solution was dried (phase separator) and evaporated. Dichloromethane (50 mL) and diethyl ether (200 mL) were added and the solid product was filtered. The product was washed twice with diethyl ether and then dried in vacuo. There was obtained 5.03 g (72%) of 4B as a solid. $^1$H NMR (500 MHz, CDCl$_3$): δ 3.13 (s, 3H), 3.90 (s, 3H), 4.42 (dd, 1H), 4.64 (dd, 1H), 4.86 (dd, 1H), 5.11 (dd, 1H), 5.40 (m, 1H), 7.02 (d, 2H), 8.09 (d, 2H), MS (APCI+) m/z 354 [M+H]$^+$.

4. (3-(4-(2-Oxa-6-azaspiro[3.3]heptan-6-ylmethyl) phenoxy)azetidin-1-yl)(5-(4-methoxyphenyl)-1,3,4-oxadiazol-2-yl)methanone 2A (0.41 g, 2.00 mmol) was dissolved in dry DMF (10 mL) and 4B (0.92 g, 2.60 mmol) was added followed by Cs$_2$CO$_3$ (1.30 g, 4.00 mmol). The reaction mixture was stirred at 90° C. for 24 h. The mixture was evaporated to near dryness and dimethylsulfoxide (10 mL) was added. The mixture was filtered and purified by preparative RP HPLC (gradient: 15-55% acetonitrile over 30 min, 0.2% ammonia buffer). The pure fractions were combined and concentrated. Dichloromethane was added and the solution was dried (phase separator) and concentrated in vacuo to give 0.26 g of a pale yellow solid. The product was further purified using flash chromatography starting with EtOAc and then eluting the product with dichloromethane/methanol containing 2 M NH$_3$ (20:1). There was obtained 0.20 g (22%) of the desired product as a solid. $^1$H NMR (500 MHz, CDCl$_3$): δ 3.35 (s, 4H), 3.47 (s, 2H), 3.87 (s, 3H), 4.30 (d, 1H), 4.62 (dd, 1H), 4.72 (s, 5H), 5.04 (m, 1H), 5.09 (dd, 1H), 6.71 (d, 2H), 7.00 (d, 2H), 7.17 (d, 2H), 8.07 (d, 2H), MS (APCI+) m/z 463 [M+H]$^+$, LC purity: 95%.

A slurry experiment was performed by weighing 15 mg of Example 4 into a vial and adding ethanol (2400 μL). The slurry was shaken for 7 days at ambient temperature and then crystals were collected using a small spatula. The crystals were dried in a hood for one hour and then analyzed using DSC (differential scanning calorimetry). A sample was weighed into an aluminium pan with a pierced lid and heated from 0° C. to 300° C. with a ramp of 5° C./min and modulated with the amplitude of ±0.6° C. every 45 second. The instrument was purged with nitrogen at 50 mL/minute; melting point 152±5° C.

Example 5

(3-(4-(2-Oxa-6-azaspiro[3.3]heptan-6-ylmethyl)phenylthio)azetidin-1-yl)(5-phenyl-1,3,4-oxadiazol-2-yl)methanone

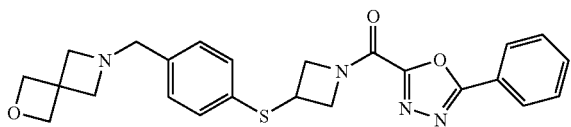

5A. (3-(4-(Hydroxymethyl)phenylthio)azetidin-1-yl)(5-phenyl-1,3,4-oxadiazol-2-yl)methanone

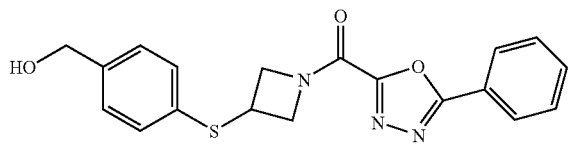

(4-Mercaptophenyl)methanol (2.38 g, 17.0 mmol) and 1C (5.00 g, 15.5 mmol) were mixed in DMF (80 mL). Cs$_2$CO$_3$ (6.05 g, 18.56 mmol) was added. The mixture was stirred at 90° C. overnight and then cooled room temperature. Ethyl acetate (150 mL) was added and the mixture was washed with water (50 mL). The aqueous layer was extracted with ethyl acetate (100 mL). The organic phases were combined, dried (MgSO$_4$) and evaporated to dryness. The residue was purified by column chromatography eluting with ethyl acetate/heptane (20:80, 40:60 and then 60:40). There was obtained 3.5 g (61%) of 5A as a solid. $^1$H NMR (500 MHz, CDCl$_3$): δ 4.19 (m, 2H), 4.64 (m, 2H), 4.69 (s, 2H), 5.10 (m, 1H), 7.34 (m, 4H), 7.53 (t, 2H), 7.59 (t, 1H), 8.15 (d, 2H), MS (APCI+) m/z 368 [M−H]$^-$.

5B. (3-(4-(Chloromethyl)phenylthio)azetidin-1-yl)(5-phenyl-1,3,4-oxadiazol-2-yl)methanone

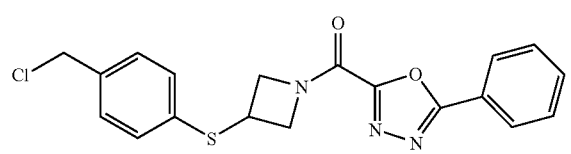

5A (3.48 g, 9.47 mmol) was dissolved in dichloromethane (150 mL) and the mixture was cooled in an ice bath. While stirring, thionyl chloride (0.76 mL, 10.4 mmol) was added dropwise. The cooling bath was removed after 30 min. The mixture was stirred for 2.5 h and then evaporated to dryness. The residue was purified by column chromatography eluting with dichloromethane. There was obtained 2.93 g (80%) of 5B as a solid. $^1$H NMR (500 MHz, CDCl$_3$): δ 4.22 (m, 2H), 4.57 (s, 2H), 4.65 (m, 2H), 5.14 (m, 1H), 7.29 (d, 2H), 7.36 (d, 2H), 7.53 (t, 2H), 7.59 (t, 1H), 8.16 (d, 2H), MS (APCI+) m/z 386 [M+H]$^+$.

5. (3-(4-(2-Oxa-6-azaspiro[3.3]heptan-6-ylmethyl)phenylthio)azetidin-1-yl)(5-phenyl-1,3,4-oxadiazol-2-yl)methanone 2-Oxa-6-azaspiro[3.3]heptane hemioxalate—for preparation, see e.g. *Angew. Chem. Int. Ed.*, 47, 4512-4515 (2008)—(0.18 g, 1.24 mmol) and 5B (0.24 g, 0.62 mmol) were mixed in DMF (5 mL). N-Ethyl-N-isopropylpropan-2-amine (0.36 mL, 2.05 mmol) was added. The mixture was stirred at room temperature for 1.5 h and then methanol (5 mL) was added. The mixture was stirred for 3 days at room temperature and then evaporated to dryness. The residue was purified by preparative RP HPLC using a gradient of 20-95% acetonitrile in water, acetonitrile, ammonia (95/5/0.2) buffer over 25 minutes. The product was further purified by column chromatography eluting with ammonia in methanol (2M)/dichloromethane (0.5-2%). There was obtained 59 mg (21%) of the desired product as a solid. $^1$H NMR (500 MHz, CDCl$_3$): δ 3.36 (s, 4H), 3.50 (s, 2H), 4.17 (m, 2H), 4.61 (m, 2H), 4.72 (s, 4H), 5.08 (m, 1H), 7.20 (d, 2H), 7.26 (d, 2H), 7.50 (t, 2H), 7.57 (t, 1H), 8.13 (d, 2H), MS (APCI+) m/z 449 [M+H]$^+$, LC purity: 93%.

Example 6

(3-(4-(2-Oxa-6-azaspiro[3.3]heptan-6-ylmethyl)phenoxy)azetidin-1-yl)(5-(4-fluorophenyl)-1,3,4-oxadiazol-2-yl)methanone

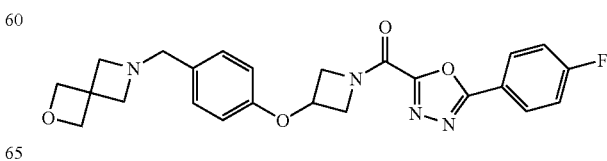

To a solution of ethyl 5-(4-fluorophenyl)-1,3,4-oxadiazole-2-carboxylate (55 mg, 0.23 mmol) in MeOH (3 mL) was added a solution of 3B (55 mg, 0.21 mmol) in MeOH (3 mL). Sodium cyanide (4 mg) was added and the reaction mixture was stirred at RT for 3 h. The mixture was transferred to a separatory funnel and diluted with DCM (50 mL). The organic layer was washed with an aqueous solution of $Na_2CO_3$, dried (phase separator) and then evaporated. The crude product was purified by flash column chromatography, first eluting with ethyl acetate and then eluting with a mixture of DCM and MeOH, which contained 2M $NH_3$ (20:1). There was obtained 75 mg (79%) of 6 as a solid. $^1$H NMR (500 MHz, $CDCl_3$): δ 3.37 (s, 4H), 3.48 (s, 2H), 4.32 (dd, 1H), 4.64 (dd, 1H), 4.75 (s, 5H), 5.06 (m, 1H), 5.10 (m, 1H), 6.72 (d, 2H), 7.22 (m, 4H), 8.17 (m, 2H), MS (APCI+) m/z 451 [M+H]$^-$. LC purity: 92%.

A slurry experiment was performed by weighing 2.7 mg of Example 6 into a vial and adding ethanol (43 µL). The slurry was shaken for 7 days at ambient temperature and then crystals were collected using a small spatula. The crystals were dried in a hood for one hour and then analyzed using DSC (differential scanning calorimetry). A sample was weighed into an aluminium pan with a pierced lid and heated from 0° C. to 300° C. with a ramp of 5° C./min and modulated with the amplitude of ±0.6° C. every 45 second. The instrument was purged with nitrogen at 50 mL/minute; melting point 117±5° C.

Example 7

(3-(4-(2-Oxa-6-azaspiro[3.3]heptan-6-ylmethyl)phenoxy)azetidin-1-yl)(5-(4-(difluoromethoxy)phenyl)-1,3,4-oxadiazol-2-yl)methanone 4-Difluoromethoxy benzoic acid hydrazide (2.0 g, 9.9 mmol) was mixed with DCM (40 mL) and triethylamine (1.80 g, 17.8 mmol). The mixture was cooled with an ice-bath and then ethyl oxalyl chloride (1.42 g, 10.4 mmol) was added during a period of 10 min. The reaction mixture was stirred at RT for 2 h and then washed with saturated aqueous $NaHCO_3$. The organic solution was dried (phase separator) and then concentrated. The residue was dissolved in toluene (40 mL) and then pyridine (0.96 g, 12.1 mmol) was added. Thionyl chloride (3.6 g, 30.2 mmol) was added dropwise over a period of 5 min. The mixture was boiled under reflux for 2.5 h. The solvent was removed by evaporation and the residue was dissolved in DCM (60 mL). The solution was washed twice with aqueous $NaHCO_3$ and then with water. The organic phase was dried over $MgSO_4$ and the solvent was removed by evaporation. There was obtained 2.50 g (73%) of 7A as a solid. $^1$H NMR (500 MHz, $CDCl_3$): δ 1.48 (t, 3H), 4.56 (m, 2H), 6.64 (t, 1H), 7.28 (d, 2H), 8.19 (d, 2H).

7. (3-(4-(2-Oxa-6-azaspiro[3.3]heptan-6-ylmethyl)phenoxy)azetidin-1-yl)(5-(4-(difluoromethoxy)phenyl)-1,3,4-oxadiazol-2-yl)methanone Using a similar protocol as described in Example 6 but employing 7A (60 mg, 0.21 mmol) and 3B (50 mg, 0.19 mmol) as starting materials afforded 65 mg (68%) of 7 as a solid. $^1$H NMR (500 MHz, $CDCl_3$): δ 3.0-4.2 (m, 6H), 4.34 (m, 1H), 4.66 (m, 1H), 4.76 (m, 5H), 5.10 (m, 2H), 6.62 (t, 1H), 6.76 (m, 2H), 7.27 (m, 4H), 8.18 (d, 2H), MS (APCI+) m/z 499 [M+H]$^+$, LC purity: 96%.

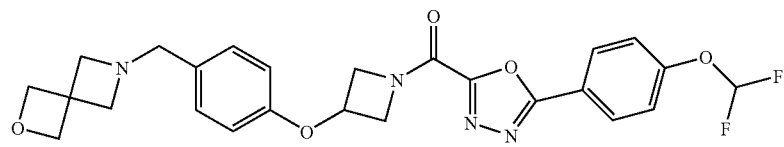

7A. Ethyl 5-(4-(difluoromethoxy)phenyl)-1,3,4-oxadiazole-2-carboxylate

Example 8

(3-(4-(2-Oxa-6-azaspiro[3.3]heptan-6-ylmethyl)-2-chlorophenoxy)azetidin-1-yl)(5-phenyl-1,3,4-oxadiazol-2-yl)methanone

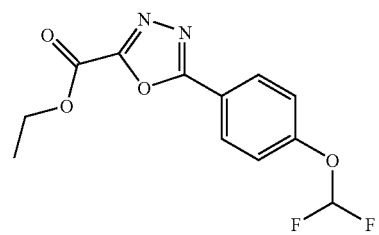

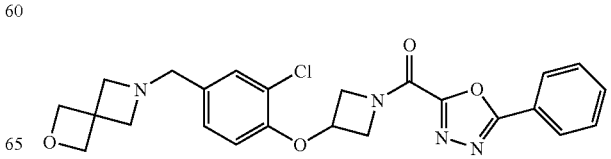

8A. 4-(2-Oxa-6-azaspiro[3.3]heptan-6-ylmethyl)-2-chlorophenol

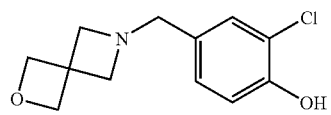

Using a similar protocol as described in Example 2A but employing 2-oxa-6-azaspiro[3.3]heptane hemi-oxalate (150 mg, 0.79 mmol) and 3-chloro-4-hydroxybenzaldehyde (160 mg, 1.02 mmol) as starting materials afforded 160 mg (84%) of 8A as an oil. $^1$H NMR (500 MHz, CD$_3$OD): δ 3.43 (s, 4H), 3.48 (s, 2H), 4.72 (s, 4H), 6.86 (d, 1H), 7.03 (d, 1H), 7.22 (s, 1H).

8B. 1-(5-Phenyl-1,3,4-oxadiazole-2-carbonyl)azetidin-3-yl 4-methylbenzenesulfonate

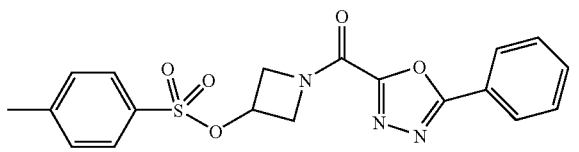

Using a similar protocol as described in Example 2C but employing 1B (250 mg, 1.02 mmol) and 4-methylbenzene-1-sulfonyl chloride (250 mg, 1.31 mmol) as starting materials afforded 365 mg (90%) of 8B as a solid. $^1$H NMR (500 MHz, CDCl$_3$): δ 2.49 (s, 3H), 4.24 (dd, 1H), 4.47 (dd, 1H), 4.72 (dd, 1H), 4.98 (dd, 1H), 5.22 (m, 1H), 7.41 (d, 2H), 7.53 (t, 2H), 7.59 (t, 1H), 7.82 (d, 2H), 8.14 (d, 2H).

8. (3-(4-(2-Oxa-6-azaspiro[3.3]heptan-6-ylmethyl)-2-chlorophenoxy)azetidin-1-yl)(5-phenyl-1,3,4-oxadiazol-2-yl)methanone Using a similar protocol as described in Example 2 but employing 8A (130 mg, 0.54 mmol) and 8B (220 mg, 0.55 mmol) as starting materials afforded 130 mg (51%) of 8 as a gum. $^1$H NMR (500 MHz, CD$_3$OD): δ 3.38 (s, 4H), 3.48 (s, 2H), 4.25 (dd, 1H), 4.6-4.8 (m, 6H), 5.15 (m, 2H), 6.78 (d, 1H), 7.15 (d, 1H), 7.32 (s, 1H), 7.56 (t, 2H), 7.61 (t, 1H), 8.09 (d, 2H), MS (APCI+) m/z 467 [M+H]$^+$, LC purity: 91%.

Example 9

(3-(4-((3,3-Dimethyl-1-oxa-6-azaspiro[3.3]heptan-6-yl)methyl)phenoxy)azetidin-1-yl)(5-(4-methoxyphenyl)-1,3,4-oxadiazol-2-yl)methanone

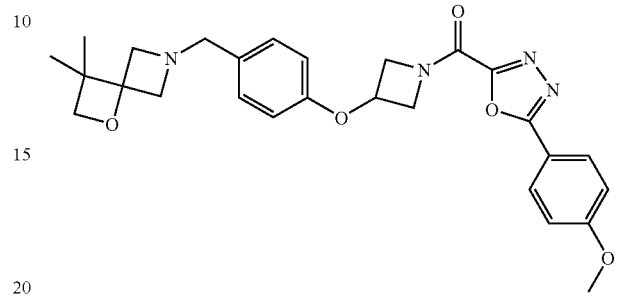

9A. 4-(1-(5-(4-methoxyphenyl)-1,3,4-oxadiazole-2-carbonyl)azetidin-3-yloxy)benzaldehyde

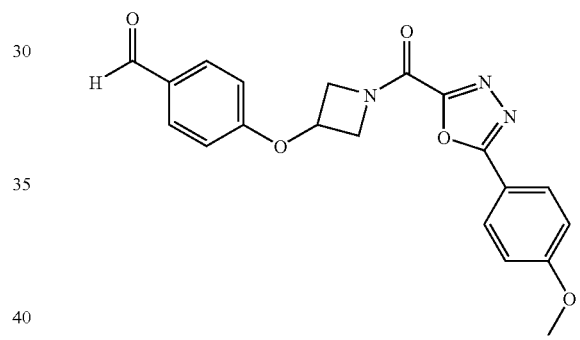

4-Hydroxybenzaldehyde (1.10 g, 9.17 mmol), cesium carbonate (3.49 g, 10.70 mmol) and 4B (2.70 g, 7.64 mmol) were mixed with DMF (80 mL). The mixture was stirred at 110° C. for 18 h then cooled to RT. The solids were filtered off and the filtrate was evaporated. The residue was treated with methanol and the solid formed was collected by filtration. Drying under vacuum gave 1.8 g (62%) of 9A as a beige solid. $^1$H NMR (500 MHz, DMSO-d$_6$): δ 3.85 (s, 3H), 4.13 (dd, 1H), 4.57 (dd, 1H), 4.65 (dd, 1H), 5.12 (dd, 1H), 5.29 (m, 1H), 7.10 (d, 2H), 7.16 (d, 2H), 7.90 (d, 2H), 8.00 (d, 2H), 9.90 (s, 1H), MS (APCI+) m/z 380 [M+H]$^+$.

9. (3-(4-((3,3-Dimethyl-1-oxa-6-azaspiro[3.3]heptan-6-yl)methyl)phenoxy)azetidin-1-yl)(5-4-methoxpheyl)-1,3,4-oxadiazol-2-yl)methanone To a solution of 9A (217 mg, 0.57 mmol) in DCM (10 mL) was added 3,3-dimethyl-1-oxa-6-azaspiro[3.3]heptan 2,2,2-trifluoroacetate (179 mg, 0.74 mmol) and triethylamine (0.20 mL, 1.44 mmol). Sodium triacetoxyborohydride (140 mg, 0.66 mmol) was added and the reaction mixture was stirred at RT for 3 days. The mixture was washed with saturated aqueous NaHCO$_3$ solution. The organic layer was filtered through a phase separator and then evaporated. The product was purified by preparative chromatography on a Kromasil C8 column using a mixture of acetonitrile and an aqueous solution of acetic acid (0.2%) as the mobile phase. Product fractions were combined and most of the acetonitrile was removed by evaporation. The aqueous residue was freeze-dried. There was obtained 165 mg (59%) of 9 as a solid. $^1$H NMR (500 MHz, CDCl$_3$): δ 1.24 (s, 6H), 3.15 (d, 2H), 3.59 (s, 2H), 3.69 (d, 2H), 3.89 (s, 3H), 4.17 (s, 2H), 4.33 (m, 1H), 4.63 (m, 1H), 4.74 (m, 1H), 5.06-5.12 (m, 2H), 6.73 (d, 2H), 7.23 (d, 2H), 7.27 (d, 2H), 8.10 (d, 2H), MS (APCI+) m/z 491 [M+H]$^+$. LC purity: 95%.

Example 10

(3-(2-Chloro-4-((3,3-dimethyl-1-oxa-6-azaspiro[3.3]heptan-6-yl)methyl)phenoxy)azetidin-1-yl)(5-phenyl-1,3,4-oxadiazol-2-yl)methanone

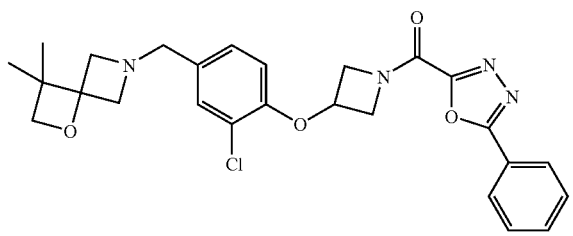

10A. 3-Chloro-4-(1-(5-phenyl-1,3,4-oxadiazole-2-carbonyl)azetidin-3-yloxy)benzaldehyde

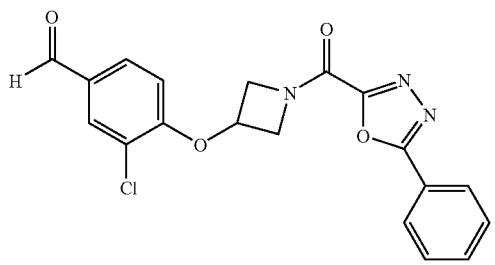

Using a similar protocol as described in Example 9A but employing 1C (500 mg, 1.55 mmol) and 3-chloro-4-hydroxybenzaldehyde (250 mg, 1.60 mmol) as starting materials gave 205 mg (34%) of 10A as a solid. $^1$H NMR (500 MHz, CD$_3$OD): δ 4.33 (m, 1H), 4.6-4.9 (m, 2H), 5.23 (m, 1H), 5.36 (m, 1H), 7.07 (d, 1H), 7.5-7.7 (m, 3H), 7.8-9.0 (m, 4H), 9.86 (s, 1H).

10. (3-(2-Chloro-4-((3,3-dimethyl-1-oxa-6-azaspiro[3.3]heptan-6-yl)methyl)phenoxy)azetidin-1-yl)(5-phenyl-1,3,4-oxadiazol-2-methanone Using a similar protocol as described in Example 9 but employing 3,3-dimethyl-1-oxa-6-azaspiro[3.3]heptan 2,2,2-trifluoroacetate (125 mg, 0.52 mmol) and 10A (100 mg, 0.26 mmol) as starting materials gave 95 mg (74%) of 10 as a solid. $^1$H NMR (500 MHz, CDCl$_3$): δ 1.24 (s, 6H), 3.11 (d, 2H), 3.51 (s, 2H), 3.62 (d, 2H), 4.17 (s, 2H), 4.41 (m, 1H), 4.66 (m, 1H), 4.82 (m, 1H), 5.1-5.2 (m, 2H), 6.60 (d, 1H), 7.13 (d, 1H), 7.35 (s, 1H), 7.4-7.7 (m, 3H), 8.15 (d, 2H), MS (APCI+) m/z 495 [M+H]$^+$, LC purity: 97%.

The invention claimed is:

1. A compound of formula I

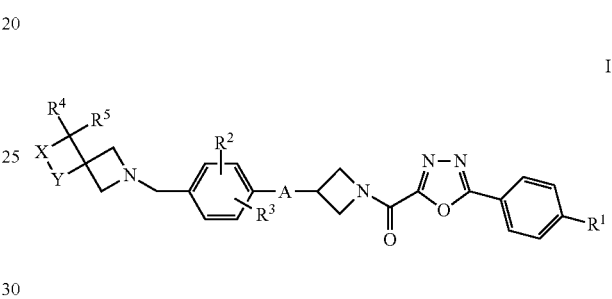

or a pharmaceutically acceptable salt thereof in which

R$^1$ represents H, fluoro, chloro, bromo, cyano, a C$_{1-3}$alkyl group optionally substituted by one or more fluoro, or a C$_{1-2}$alkoxy group optionally substituted by one or more fluoro;

A represents O or S;

R$^2$ and R$^3$ independently represent H, fluoro, chloro, bromo, a C$_{1-4}$alkyl group optionally substituted by one or more fluoro, or a C$_{1-4}$alkoxy group optionally substituted by one or more fluoro; provided that R$^2$ and R$^3$ are not located meta to each other;

R$^4$ and R$^5$ independently represent H or a C$_{1-4}$alkyl group; and

X and Y independently represent O or CH$_2$ with the proviso that X and Y are different.

2. The compound as claimed in claim 1 of formula IA

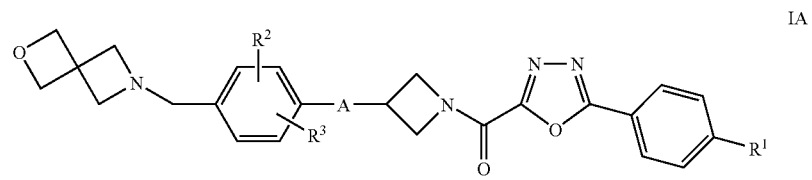

or a pharmaceutically acceptable salt thereof in which

R$^1$ represents H, fluoro, chloro, bromo, cyano a C$_{1-3}$alkyl group optionally substituted by one or more fluoro, or a C$_{1-2}$alkoxy group optionally substituted by one or more fluoro;

A represents O or S; and

R² and R³ independently represent H, fluoro, chloro, bromo, a C₁₋₄alkyl group optionally substituted by one or more fluoro, or a C₁₋₄alkoxy group optionally substituted by one or more fluoro; provided that R² and R³ are not located meta to each other.

3. The compound as claimed in claim 1 of formula IB

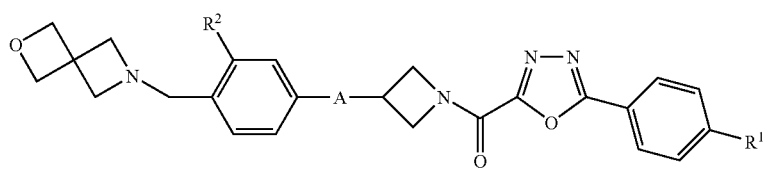

IB or a pharmaceutically acceptable salt thereof in which
R¹ represents H, chloro or a C₁₋₂alkoxy group optionally substituted by one or more fluoro;
A represents O or S; and
R² represents H or chloro.

4. The compound as claimed in claim 1 of formula IC

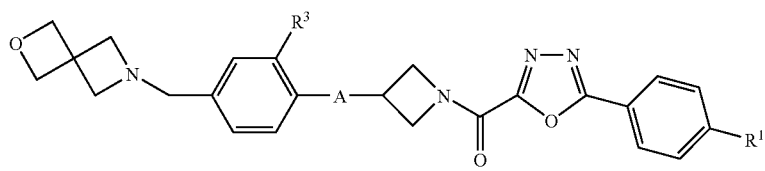

IC or a pharmaceutically acceptable salt thereof in which
R¹ represents H, chloro or a C₁₋₂alkoxy group optionally substituted by one or more fluoro;
A represents O or S; and
R³ represents H or chloro.

5. The compound as claimed in claim 1 of formula ID

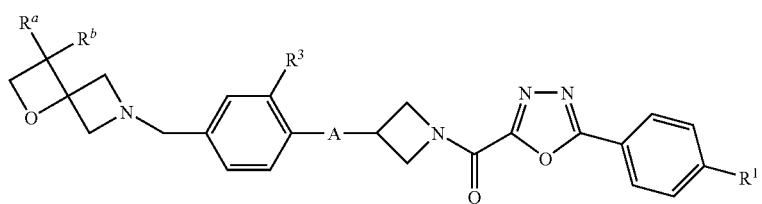

ID or a pharmaceutically acceptable salt thereof in which
Rᵃ and Rᵇ independently represent H or a C₁₋₄alkyl group;
R¹ represents H, chloro or a C₁₋₂alkoxy group optionally substituted by one or more fluoro;
A represents O or S; and
R³ represents H or chloro.

6. The compound as claimed in claim 1 in which A represents O.

7. The compound as claimed in claim 1 in which A represents S.

8. The compound as claimed in claim 1 selected from:
(3-(4-(2-oxa-6-azaspiro[3.3]heptan-6-ylmethyl)-3-chlorophenoxy)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-chlorophenyl)-1,3,4-oxadiazol-2-yl)methanone;
(3-(4-(2-oxa-6-azaspiro[3.3]heptan-6-ylmethyl)phenoxy)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-methoxyphenyl)-1,3,4-oxadiazol-2-yl)methanone;
(3-(4-(2-oxa-6-azaspiro[3.3]heptan-6-ylmethyl)phenylthio)azetidin-1-yl)(5-phenyl-1,3,4-oxadiazol-2-yl)methanone;
(3-(4-(2-oxa-6-azaspiro[3.3]heptan-6-ylmethyl)phenoxy)azetidin-1-yl)(5-(4-fluorophenyl)-1,3,4-oxadiazol-2-yl)methanone;
(3-(4-(2-oxa-6-azaspiro[3.3]heptan-6-ylmethyl)phenoxy)azetidin-1-yl)(5-(4-(difluoromethoxy)phenyl)-1,3,4-oxadiazol-2-yl)methanone;
(3-(4-(2-oxa-6-azaspiro[3.3]heptan-6-ylmethyl)-2-chlorophenoxy)azetidin-1-yl)(5-phenyl-1,3,4-oxadiazol-2-yl)methanone;
(3-(4-((3,3-dimethyl-1-oxa-6-azaspiro[3.3]heptan-6-yl)methyl)phenoxy)azetidin-1-yl)(5-(4-methoxyphenyl)-1,3,4-oxadiazol-2-yl)methanone; and
(3-(2-chloro-4-((3,3-dimethyl-1-oxa-6-azaspiro[3.3]heptan-6-yl)methyl)phenoxy)azetidin-1-yl)(5-phenyl-1,3,4-oxadiazol-2-yl)methanone;
and pharmaceutically acceptable salts thereof.

9. A pharmaceutical composition comprising a compound according to claim 1 or claim 8 and a pharmaceutically acceptable carrier and/or diluent.

10. A method for treatment of a disease or condition in which modulation of the MCH1 receptor is beneficial comprising administering to a warm-blooded animal in need of such treatment a therapeutically-effective amount of a compound in accordance with claim 1, wherein said disease or condition is selected from the group consisting of anxiety, obesity, and depression.

11. The method according to claim 10 wherein said disease or condition is obesity.

12. A method for the treatment of a disease or condition in which modulation of the H3 receptor is beneficial comprising administering to a warm-blooded animal in need of such treatment a therapeutically-effective amount of a compound in accordance with claim 1, wherein the disease or condition is selected from the group consisting of cognitive deficiency in schizophrenia, narcolepsy, obesity, Attention deficit hyperactivity disorder, pain and Alzheimer's disease.

13. A process for the preparation of a compound of formula I according to claim 1 comprising
a) reacting a compound of formula II

in which A, X, Y, $R^2$, $R^3$, $R^4$ and $R^5$ are as defined in claim 1 with a compound of formula III

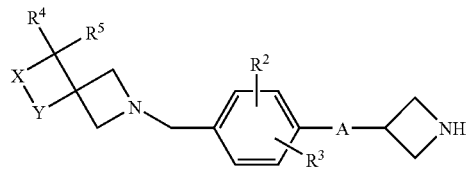

in which $R^1$ is as defined in claim 1 and $L_1$ represents a leaving group which is a $C_{1-4}$alkoxy group, optionally in the presence of a solvent at a temperature in the range of 0 to 150 ° C.; or
b) reacting a compound of formula IV

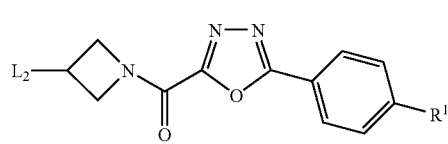

in which A, X, Y, $R^2$, $R^3$, $R^4$ and $R^5$ are as defined in claim 1 with a compound of formula V

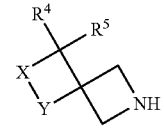

in which $R^1$ is as defined in claim 1 and $L_2$ represents a leaving group selected from the group consisting of mesyloxy and tosyloxy in the presence of a base optionally in the presence of a solvent at a temperature in the range of 0 to 150 ° C.; or
c) reacting a compound of formula VI

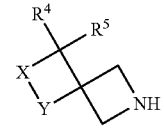

in which X, Y, $R^4$ and $R^5$ are as defined in claim 1 with a compound of formula VII

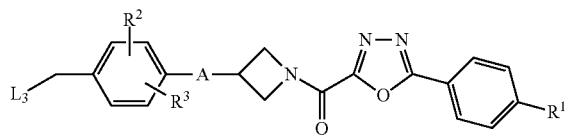

in which $R^1$, $R^2$, $R^3$ and A are as defined in claim 1 and $L_3$ represents a leaving group selected from the group consisting of chloro, bromo, iodo and fluoro, optionally in the presence of a solvent and optionally in the presence of a base at a temperature in the range of 0 to 150 ° C.; or
d) reacting a compound of formula VI

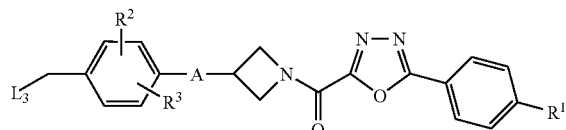

in which X, Y, $R^4$ and $R^5$ are as defined in claim 1 with a compound of formula XII

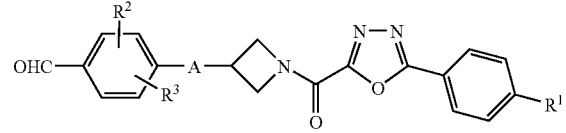

in which $R^1$, $R^2$, $R^3$ and A are as defined in claim 1 in the presence of a reducing agent in an appropriate solvent.

14. The compound as claimed in claim 8 which is (3-(4-(2-oxa-6-azaspiro[3.3]heptan-6-ylmethyl)-3-chlorophenoxy)azetidin-1-yl)(5-phenyl-1,3,4-oxadiazol-2-yl)methanone or a pharmaceutically acceptable salt thereof.

15. The compound as claimed in claim 8 which is (3-(4-(2-oxa-6-azaspiro[3.3]heptan-6-ylmethyl)phenoxy)azetidin-1-yl)(5-(4-chlorophenyl)-1,3,4-oxadiazol-2-yl)methanone or a pharmaceutically acceptable salt thereof.

16. The compound as claimed in claim 8 which is (3-(4-(2-oxa-6-azaspiro[3.3]heptan-6-ylmethyl)phenoxy)azetidin-1-yl)(5-phenyl-1,3,4-oxadiazol-2-yl)methanone or a pharmaceutically acceptable salt thereof.

17. The compound as claimed in claim 8 which is (3-(4-(2-oxa-6-azaspiro[3.3]heptan-6-ylmethyl)phenoxy)azetidin-1-yl)(5-(4-methoxyphenyl)-1,3,4-oxadiazol-2-yl)methanone or a pharmaceutically acceptable salt thereof.

18. The compound as claimed in claim 8 which is (3-(4-(2-oxa-6-azaspiro[3.3]heptan-6-ylmethyl)phenylthio)azetidin-1-yl)(5-phenyl-1,3,4oxadiazol-2-yl)methanone or a pharmaceutically acceptable salt thereof.

19. The compound as claimed in claim 8 which is (3-(4-(2-oxa-6-azaspiro[3.3]heptan-6-ylmethyl)phenoxy)azetidin-1-yl)(5-(4-fluorophenyl)-1,3,4-oxadiazol-2-yl)methanone or a pharmaceutically acceptable salt thereof.

20. The compound as claimed in claim 8 which is (3-(4-(2-oxa-6-azaspiro[3.3]heptan-6-ylmethyl)phenoxy)azetidin-1-yl)(5-(4-(difluoromethoxy)phenyl)-1,3,4-oxadiazol-2-yl)methanone or a pharmaceutically acceptable salt thereof.

21. The compound as claimed in claim 8 which is (3-(4-(2-oxa-6-azaspiro[3.3]heptan-6-ylmethyl)-2-chlorophenoxy)azetidin-1-yl)(5-phenyl-1,3,4-oxadiazol-2-yl)methanone or a pharmaceutically acceptable salt thereof.

22. The compound as claimed in claim 8 which is (3-(4-((3,3-dimethyl-1-oxa-6-azaspiro[3.3]heptan-6-yl)methyl)phenoxy)azetidin-1-yl)(5-(4-methoxyphenyl)-1,3,4-oxadiazol-2-yl)methanone or a pharmaceutically acceptable salt thereof.

23. The compound as claimed in claim 8 which is (3-(2-chloro-4-((3,3-dimethyl-1-oxa-6-azaspiro[3.3]heptan-6-yl)methyl)phenoxy)azetidin-1-yl)(5-phenyl-1,3,4-oxadiazol-2-yl)methanone or a pharmaceutically acceptable salt thereof.

\* \* \* \* \*